US007601885B2

(12) United States Patent
Verdaguer et al.

(10) Patent No.: US 7,601,885 B2
(45) Date of Patent: Oct. 13, 2009

(54) TRANSGENIC PLANT COMPRISING A CASSAVA VEIN MOSAIC VIRUS PROMOTER AND A HETEROLOGOUS NUCLEIC ACID SEQUENCE

(75) Inventors: Bertrand Verdaguer, Toulouse (FR); Alexandre de Kochko, San Diego, CA (US); Roger N. Beachy, St. Louis, MO (US); Claude Fauquet, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 11/191,658

(22) Filed: Jul. 27, 2005

(65) Prior Publication Data

US 2006/0041950 A1 Feb. 23, 2006

Related U.S. Application Data

(62) Division of application No. 09/202,838, filed as application No. PCT/US97/10376 on Jun. 20, 1997, now Pat. No. 7,053,205.

(60) Provisional application No. 60/020,129, filed on Jun. 20, 1996.

(51) Int. Cl.

| | |
|---|---|
| ***C12N 15/82*** | (2006.01) |
| ***A01H 9/00*** | (2006.01) |
| ***C12Q 1/68*** | (2006.01) |
| ***C12N 15/00*** | (2006.01) |
| ***C07H 21/04*** | (2006.01) |

(52) U.S. Cl. ........................ 800/278; 435/6; 435/320.1; 435/325; 536/23.1; 536/24.1; 800/295

(58) Field of Classification Search ........................ None
See application file for complete search history.

(56) References Cited

OTHER PUBLICATIONS

Mitsuhara et al., Plant Cell Physiology, vol. 37, pp. 49-59, Jan. 1996.*
Calvert et al., Journal of General Virology, vol. 76, pp. 1271-1276, 1995.*
Database GenBank acc. 3 U20341.1, Cassava vein mosaic virus, complete genome. Oct. 25, 1995.*
Verdaguer, et al., Isolation and expression in transgenic tobacco and rice plants, of the cassava vein mosaic virus (CVMV) promoter, 1996, *Plant Mol. Biol.*, 31:1129-1139.
Calvert, et al., Characterization of cassava vein mosaic virus: a distinct plant pararetro virus, 1995, *J. General Virol*, 76:1271-1276.

* cited by examiner

*Primary Examiner*—Shubo Joe Zhou
(74) *Attorney, Agent, or Firm*—Hugh Wang; Thomas Fitting

(57) ABSTRACT

The invention relates to compositions and methods useful for the production of transgenic plants. In particular, the invention relates to cassava vein mosaic virus (CsVMV) promoter sequences and expression cassettes containing CsVMV promoter sequences. The invention describes nucleic acid molecules, vectors and transgenic plants containing promoters derived from CsVMV promoter that are operatively linked to heterologous DNA sequences, and methods for producing transgenic plants containing these promoters.

17 Claims, 12 Drawing Sheets

| GGTA CCAGAAGGTA | ATTATCCAAG | ATGTAGCATC | AAGAATCCAA |
| KpnI -400 | | | ⇓ |
| TGTTTACGGG | AAAAACTATG | GAAGTATTAT | GTGAGCTCAG |
| | -350 | | AluI |
| CAAGAAGCAG | ATCAATATGC | GGCACATATG | CAACCTATGT |
| | | -300 | |
| TCAAAAATGA | AGAATGTACA | GATACAAGAT | CCTATACTGC |
| | | | -250 |
| CAGAATACGA | AGAAGAATAC | GTAGAAATTG | AAAAAGAAGA |
| | | MNF1 | |
| ACCAGGCGAA | GAAAAGAATC | TTGAAGACGT | AAGCACTGACG |
| -200 | | AS1 | |
| ACAACAATG | AAAAGAAGAA | GATAAGGTCG | GTGATTGTGA |
| | -150 | box I | eSV40 |
| AAGAGACATA | GAGGACACAT | GTAAGGTGGA | AAATGTAAGG |
| | | -100 eSV40 | |
| GCGGAAAGTA | ACCTTATCAC | AAAGGAATCT | TATCCCCCACT |
| | | "ComYMV like" | -50 |
| ACTTATCCT | TTTATATTTT | TCCGTGTCAT | TTTTGCCCTT |
| GAGTTTCCT | ATATAAGGAA | CCAAGTTCGG | CATTTGTAA |
| +1 | TATA box | ⇓ | |
| AACAAGAAAA | AATTTGGTGT | A AGCTATTTT | CTTTGAAGTA |
| | | AluI | +72 |
| CTGAGGATAC | AAGTTCAGAG | AAATTTGTAA | GTTTGAATTC |
| | | | EcoRI |

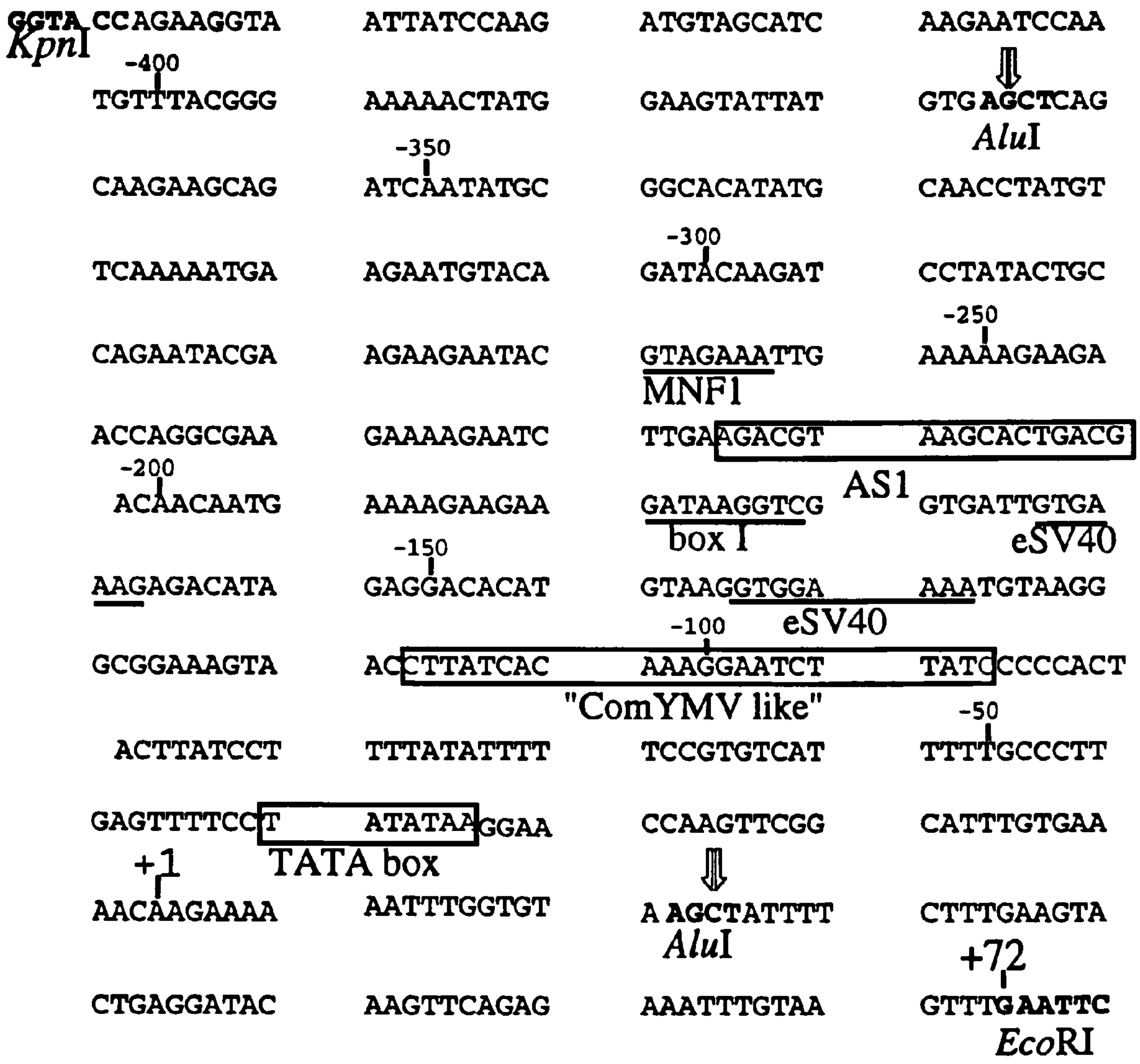

FIG. 3

SEQUENCE LISTING

```
<160> NUMBER OF SEQ ID NOS: 37

<210> SEQ ID NO 1
<211> LENGTH: 392
<212> TYPE: DNA
<213> ORGANISM: Cassava vein mosaic virus

<400> SEQUENCE: 1

agctcagcaa gaagcagatc aatatgcggc acatatgcaa cctatgttca aaaatgaaga     60

atgtacagat acaagatcct atactgccag aatacgaaga agaatacgta gaaattgaaa    120

aagaagaacc aggcgaagaa aagaatcttg aagacgtaag cactgacgac aacaatgaaa    180

agaagaagat aaggtcggtg attgtgaaag agacatagag gacacatgta aggtggaaaa    240

tgtaagggcg gaaagtaacc ttatcacaaa ggaatcttat cccccactac ttatcctttt    300

atatttttcc gtgtcatttt tgcccttgag ttttcctata taaggaacca agttcggcat    360

ttgtgaaaac aagaaaaaat ttggtgtaag ct                                  392

<210> SEQ ID NO 2
<211> LENGTH: 524
<212> TYPE: DNA
<213> ORGANISM: Cassava vein mosaic virus

<400> SEQUENCE: 2

ggtaccagaa ggtaattatc caagatgtag catcaagaat ccaatgttta cgggaaaaac     60

tatggaagta ttatgtgagc tcagcaagaa gcagatcaat atgcggcaca tatgcaacct    120

atgttcaaaa atgaagaatg tacagataca agatcctata ctgccagaat acgaagaaga    180

atacgtagaa attgaaaaag aagaaccagg cgaagaaaag aatcttgaag acgtaagcac    240

tgacgacaac aatgaaaaga agaagataag gtcggtgatt gtgaaagaga catagaggac    300

acatgtaagg tggaaaatgt aagggcggaa agtaacctta tcacaaagga atcttatccc    360

ccactactta tccttttata tttttccgtg tcatttttgc ccttgagttt tcctatataa    420

ggaaccaagt tcggcatttg tgaaaacaag aaaaaatttg gtgtaagcta ttttctttga    480

agtactgagg atacaagttc agagaaattt gtaagtttga attc                     524

<210> SEQ ID NO 3
<211> LENGTH: 524
<212> TYPE: DNA
<213> ORGANISM: Cassava vein mosaic virus

<400> SEQUENCE: 3

ggtaccagaa ggtaattatc caagatgtag catcaagaat ccaatgttta cgggaaaaac     60

tatggaagta ttatgtgagc tcagcaagaa gcagatcaat atgcggcaca tatgcaacct    120

atgttcaaaa atgaagaatg tacagataca agatcctata ctgccagaat acgaagaaga    180

atacgtagaa attgaaaaag aagaaccagg cgaagaaaag aatcttgaag acgtaagcac    240

tgacgacaac aatgaaaaga agaagataag gtcggtgatt gtgaaagaga catagaggac    300

acatgtaagg tggaaaatgt aagggcggaa agtaacctta tcacaaagga atcttatccc    360

ccactactta tccttttata tttttccgtg tcatttttgc ccttgagttt tcctatataa    420
```

-continued ggaaccaagt tcggcatttg tgaaaacaag aaaaaatttg gtgtaagcta ttttctttga 480
agtactgagg atacaagttc agagaaattt gtaagtttga attc 524

<210> SEQ ID NO 4
<211> LENGTH: 411
<212> TYPE: DNA
<213> ORGANISM: Cassava vein mosaic virus

<400> SEQUENCE: 4
ggatcctatg ttcaaaaatg aagaatgtac agatacaaga tcctatactg ccagaatacg 60
aagaagaata cgtagaaatt gaaaaagaag aaccaggcga agaaaagaat cttgaagacg 120
taagcactga cgacaacaat gaaaagaaga agataaggtc ggtgattgtg aaagagacat 180
agaggacaca tgtaaggtgg aaaatgtaag ggcggaaagt aaccttatca caaaggaatc 240
ttatccccca ctacttatcc ttttatattt ttccgtgtca tttttgccct tgagttttcc 300
tatataagga accaagttcg gcatttgtga aaacaagaaa aaatttggtg taagctattt 360
tctttgaagt actgaggata caagttcaga gaaatttgta agtttgaatt c 411

<210> SEQ ID NO 5
<211> LENGTH: 305
<212> TYPE: DNA
<213> ORGANISM: Cassava vein mosaic virus

<400> SEQUENCE: 5
ggatcctgaa gacgtaagca ctgacgacaa caatgaaaag aagaagataa ggtcggtgat 60
tgtgaaagag acatagagga cacatgtaag gtggaaaatg taagggcgga aagtaacctt 120
atcacaaagg aatcttatcc cccactactt atccttttat atttttccgt gtcatttttg 180
cccttgagtt ttcctatata aggaaccaag ttcggcattt gtgaaaacaa gaaaaaattt 240
ggtgtaagct attttctttg aagtactgag gatacaagtt cagagaaatt tgtaagtttg 300
aattc 305

<210> SEQ ID NO 6
<211> LENGTH: 261
<212> TYPE: DNA
<213> ORGANISM: Cassava vein mosaic virus

<400> SEQUENCE: 6
ggatccggtc ggtgattgtg aaagagacat agaggacaca tgtaaggtgg aaaatgtaag 60
ggcggaaagt aaccttatca caaaggaatc ttatccccca ctacttatcc ttttatattt 120
ttccgtgtca tttttgccct tgagttttcc tatataagga accaagttcg gcatttgtga 180
aaacaagaaa aaatttggtg taagctattt tctttgaagt actgaggata caagttcaga 240
gaaatttgta agtttgaatt c 261

<210> SEQ ID NO 7
<211> LENGTH: 193
<212> TYPE: DNA
<213> ORGANISM: Cassava vein mosaic virus

<400> SEQUENCE: 7
ggatccttat cacaaaggaa tcttatcccc cactacttat ccttttatat ttttccgtgt 60
catttttgcc cttgagtttt cctatataag gaaccaagtt cggcatttgt gaaaacaaga 120
aaaaatttgg tgtaagctat tttctttgaa gtactgagga tacaagttca gagaaatttg 180

-continued

```
taagtttgaa ttc                                                193

<210> SEQ ID NO 8
<211> LENGTH: 143
<212> TYPE: DNA
<213> ORGANISM: Cassava vein mosaic virus

<400> SEQUENCE: 8

ggatccgtgt catttttgcc cttgagtttt cctatataag gaaccaagtt cggcatttgt     60

gaaaacaaga aaaaatttgg tgtaagctat tttctttgaa gtactgagga tacaagttca    120

gagaaatttg taagtttgaa ttc                                            143

<210> SEQ ID NO 9
<211> LENGTH: 420
<212> TYPE: DNA
<213> ORGANISM: Cassava vein mosaic virus

<400> SEQUENCE: 9

tctagaccag aaggtaatta tccaagatgt agcatcaaga atccaatgtt tacgggaaaa     60

actatggaag tattatgtga gctcagcaag aagcagatca atatgcggca catatggatc    120

ctgaagacgt aagcactgac gacaacaatg aaaagaagaa gataaggtcg gtgattgtga    180

aagagacata gaggacacat gtaaggtgga aaatgtaagg gcggaaagta accttatcac    240

aaaggaatct tatcccccac tacttatcct tttatatttt tccgtgtcat ttttgccctt    300

gagttttcct atataaggaa ccaagttcgg catttgtgaa aacaagaaaa aatttggtgt    360

aagctatttt ctttgaagta ctgaggatac aagttcagag aaatttgtaa gtttgaattc    420

<210> SEQ ID NO 10
<211> LENGTH: 482
<212> TYPE: DNA
<213> ORGANISM: Cassava vein mosaic virus

<400> SEQUENCE: 10

tctagaccag aaggtaatta tccaagatgt agcatcaaga atccaatgtt tacgggaaaa     60

actatggaag tattatgtga gctcagcaag aagcagatca atatgcggca catatgcaac    120

ctatgttcaa aaatgaagaa tgtacagata caagatccta tactgccaga atacgaagaa    180

gaatacgtag aaattgaaaa agaagaacca ggcgaagaaa aggatccggt cggtgattgt    240

gaaagagaca tagaggacac atgtaaggtg gaaaatgtaa gggcggaaag taaccttatc    300

acaaaggaat cttatccccc actacttatc cttttatatt tttccgtgtc atttttgccc    360

ttgagttttc ctatataagg aaccaagttc ggcatttgtg aaaacaagaa aaaatttggt    420

gtaagctatt ttctttgaag tactgaggat acaagttcag agaaatttgt aagtttgaat    480

tc                                                                   482

<210> SEQ ID NO 11
<211> LENGTH: 458
<212> TYPE: DNA
<213> ORGANISM: Cassava vein mosaic virus

<400> SEQUENCE: 11

tctagaccag aaggtaatta tccaagatgt agcatcaaga atccaatgtt tacgggaaaa     60

actatggaag tattatgtga gctcagcaag aagcagatca atatgcggca catatgcaac    120

ctatgttcaa aaatgaagaa tgtacagata caagatccta tactgccaga atacgaagaa    180

gaatacgtag aaattgaaaa agaagaacca ggcgaagaaa agaatcttga agacgtaagc    240
```

-continued

```
actgacgaca acaatgaaaa gaagaggatc cttatcacaa aggaatctta tcccccacta    300

cttatccttt tatatttttc cgtgtcattt ttgcccttga gttttcctat ataaggaacc    360

aagttcggca tttgtgaaaa caagaaaaaa tttggtgtaa gctattttct ttgaagtact    420

gaggatacaa gttcagagaa atttgtaagt ttgaattc                            458
```

<210> SEQ ID NO 12
<211> LENGTH: 468
<212> TYPE: DNA
<213> ORGANISM: Cassava vein mosaic virus

<400> SEQUENCE: 12

```
tctagaccag aaggtaatta tccaagatgt agcatcaaga atccaatgtt tacgggaaaa     60

actatggaag tattatgtga gctcagcaag aagcagatca atatgcggca catatgcaac    120

ctatgttcaa aaatgaagaa tgtacagata caagatccta tactgccaga atacgaagaa    180

gaatacgtag aaattgaaaa agaagaacca ggcgaagaaa agaatcttga agacgtaagc    240

actgacgaca acaatgaaaa gaagaagata aggtcggatc cttatcacaa aggaatctta    300

tcccccacta cttatccttt tatatttttc cgtgtcattt ttgcccttga gttttcctat    360

ataaggaacc aagttcggca tttgtgaaaa caagaaaaaa tttggtgtaa gctattttct    420

ttgaagtact gaggatacaa gttcagagaa atttgtaagt ttgaattc                 468
```

<210> SEQ ID NO 13
<211> LENGTH: 491
<212> TYPE: DNA
<213> ORGANISM: Cassava vein mosaic virus

<400> SEQUENCE: 13

```
tctagaccag aaggtaatta tccaagatgt agcatcaaga atccaatgtt tacgggaaaa     60

actatggaag tattatgtga gctcagcaag aagcagatca atatgcggca catatgcaac    120

ctatgttcaa aaatgaagaa tgtacagata caagatccta tactgccaga atacgaagaa    180

gaatacgtag aaattgaaaa agaagaacca ggcgaagaaa agaatcttga agacgtaagc    240

actgacgaca acaatgaaaa gaagaagata aggtcggtga ttgtgaaaga gacatagagg    300

atccttatca caaaggaatc ttatccccca ctacttatcc ttttatattt ttccgtgtca    360

tttttgccct tgagttttcc tatataagga accaagttcg gcatttgtga aaacaagaaa    420

aaatttggtg taagctattt tctttgaagt actgaggata caagttcaga gaaatttgta    480

agtttgaatt c                                                         491
```

<210> SEQ ID NO 14
<211> LENGTH: 408
<212> TYPE: DNA
<213> ORGANISM: Cassava vein mosaic virus

<400> SEQUENCE: 14

```
tctagaccag aaggtaatta tccaagatgt agcatcaaga atccaatgtt tacgggaaaa     60

actatggaag tattatgtga gctcagcaag aagcagatca atatgcggca catatgcaac    120

ctatgttcaa aaatgaagaa tgtacagata caagatccta tactgccaga atacgaagaa    180

gaatacgtag aaattgaaaa agaagaacca ggcgaagaaa agaatcttga agacgtaagc    240

actgacgaca acaatgaaaa gaagaggatc cgtgtcattt ttgcccttga gttttcctat    300

ataaggaacc aagttcggca tttgtgaaaa caagaaaaaa tttggtgtaa gctattttct    360
```

-continued

```
ttgaagtact gaggatacaa gttcagagaa atttgtaagt ttgaattc              408


<210> SEQ ID NO 15
<211> LENGTH: 418
<212> TYPE: DNA
<213> ORGANISM: Cassava vein mosaic virus

<400> SEQUENCE: 15

tctagaccag aaggtaatta tccaagatgt agcatcaaga atccaatgtt tacgggaaaa    60

actatggaag tattatgtga gctcagcaag aagcagatca atatgcggca catatgcaac   120

ctatgttcaa aaatgaagaa tgtacagata caagatccta tactgccaga atacgaagaa   180

gaatacgtag aaattgaaaa agaagaacca ggcgaagaaa agaatcttga agacgtaagc   240

actgacgaca acaatgaaaa gaagaagata aggtcggatc cgtgtcattt ttgcccttga   300

gttttcctat ataaggaacc aagttcggca tttgtgaaaa caagaaaaaa tttggtgtaa   360

gctattttct ttgaagtact gaggatacaa gttcagagaa atttgtaagt ttgaattc     418


<210> SEQ ID NO 16
<211> LENGTH: 441
<212> TYPE: DNA
<213> ORGANISM: Cassava vein mosaic virus

<400> SEQUENCE: 16

tctagaccag aaggtaatta tccaagatgt agcatcaaga atccaatgtt tacgggaaaa    60

actatggaag tattatgtga gctcagcaag aagcagatca atatgcggca catatgcaac   120

ctatgttcaa aaatgaagaa tgtacagata caagatccta tactgccaga atacgaagaa   180

gaatacgtag aaattgaaaa agaagaacca ggcgaagaaa agaatcttga agacgtaagc   240

actgacgaca acaatgaaaa gaagaagata aggtcggtga ttgtgaaaga gacatagagg   300

atccgtgtca tttttgccct tgagttttcc tatataagga accaagttcg gcatttgtga   360

aaacaagaaa aaatttggtg taagctattt tctttgaagt actgaggata caagttcaga   420

gaaatttgta agtttgaatt c                                             441


<210> SEQ ID NO 17
<211> LENGTH: 476
<212> TYPE: DNA
<213> ORGANISM: Cassava vein mosaic virus

<400> SEQUENCE: 17

tctagaccag aaggtaatta tccaagatgt agcatcaaga atccaatgtt tacgggaaaa    60

actatggaag tattatgtga gctcagcaag aagcagatca atatgcggca catatgcaac   120

ctatgttcaa aaatgaagaa tgtacagata caagatccta tactgccaga atacgaagaa   180

gaatacgtag aaattgaaaa agaagaacca ggcgaagaaa agaatcttga agacgtaagc   240

actgacgaca acaatgaaaa gaagaagata aggtcggtga ttgtgaaaga gacatagagg   300

acacatgtaa ggtggaaaat gtaagggcgg aaaggatccg tgtcattttt gcccttgagt   360

tttcctatat aaggaaccaa gttcggcatt tgtgaaaaca agaaaaaatt tggtgtaagc   420

tattttcttt gaagtactga ggatacaagt tcagagaaat ttgtaagttt gaattc       476


<210> SEQ ID NO 18
<211> LENGTH: 31
<212> TYPE: DNA
<213> ORGANISM: Artificial Sequence
<220> FEATURE:
<223> OTHER INFORMATION: Synthesized
```

-continued

<400> SEQUENCE: 18
accggtacca gaaggtaatt atccaagatg t 31

<210> SEQ ID NO 19
<211> LENGTH: 30
<212> TYPE: DNA
<213> ORGANISM: Artificial Sequence
<220> FEATURE:
<223> OTHER INFORMATION: Synthesized

<400> SEQUENCE: 19
cggaattcaa acttacaaat ttctctgaag 30

<210> SEQ ID NO 20
<211> LENGTH: 34
<212> TYPE: DNA
<213> ORGANISM: Artificial Sequence
<220> FEATURE:
<223> OTHER INFORMATION: Synthesized

<400> SEQUENCE: 20
cgcgatccag actgaatgcc cacaggccgt cgag 34

<210> SEQ ID NO 21
<211> LENGTH: 17
<212> TYPE: DNA
<213> ORGANISM: Cassava vein mosaic virus

<400> SEQUENCE: 21
agacgtaagc actgacg 17

<210> SEQ ID NO 22
<211> LENGTH: 22
<212> TYPE: DNA
<213> ORGANISM: Cassava vein mosaic virus

<400> SEQUENCE: 22
cttatcacaa aggaatctta tc 22

<210> SEQ ID NO 23
<211> LENGTH: 22
<212> TYPE: DNA
<213> ORGANISM: Cassava vein mosaic virus

<400> SEQUENCE: 23
cttatcacaa aggaatctta tc 22

<210> SEQ ID NO 24
<211> LENGTH: 28
<212> TYPE: DNA
<213> ORGANISM: Artificial Sequence
<220> FEATURE:
<223> OTHER INFORMATION: Synthesized

<400> SEQUENCE: 24
gctctagacc agaaggtaat tatccaag 28

<210> SEQ ID NO 25
<211> LENGTH: 26
<212> TYPE: DNA
<213> ORGANISM: Artificial Sequence
<220> FEATURE:
<223> OTHER INFORMATION: Synthesized -continued

<400> SEQUENCE: 25
tatggatcct atgttcaaaa atgaag 26

<210> SEQ ID NO 26
<211> LENGTH: 26
<212> TYPE: DNA
<213> ORGANISM: Artificial Sequence
<220> FEATURE:
<223> OTHER INFORMATION: Synthesized

<400> SEQUENCE: 26
aaaggatcct gaagacgtaa gcactg 26

<210> SEQ ID NO 27
<211> LENGTH: 25
<212> TYPE: DNA
<213> ORGANISM: Artificial Sequence
<220> FEATURE:
<223> OTHER INFORMATION: Synthesized

<400> SEQUENCE: 27
agaggatccg gtcggtgatt gtgaa 25

<210> SEQ ID NO 28
<211> LENGTH: 25
<212> TYPE: DNA
<213> ORGANISM: Artificial Sequence
<220> FEATURE:
<223> OTHER INFORMATION: Synthesized

<400> SEQUENCE: 28
aaaggatcct tatcacaaag gaatc 25

<210> SEQ ID NO 29
<211> LENGTH: 27
<212> TYPE: DNA
<213> ORGANISM: Artificial Sequence
<220> FEATURE:
<223> OTHER INFORMATION: Synthesized

<400> SEQUENCE: 29
tatggatccg tgtcattttt gcccttg 27

<210> SEQ ID NO 30
<211> LENGTH: 29
<212> TYPE: DNA
<213> ORGANISM: Artificial Sequence
<220> FEATURE:
<223> OTHER INFORMATION: Synthesized

<400> SEQUENCE: 30
cggaattcaa acttacaaat ttctctaag 29

<210> SEQ ID NO 31
<211> LENGTH: 25
<212> TYPE: DNA
<213> ORGANISM: Artificial Sequence
<220> FEATURE:
<223> OTHER INFORMATION: Synthesized

<400> SEQUENCE: 31
taaggatcct ttccgccctt acatt 25

<210> SEQ ID NO 32
<211> LENGTH: 25

-continued

```
<212> TYPE: DNA
<213> ORGANISM: Artificial Sequence
<220> FEATURE:
<223> OTHER INFORMATION: Synthesized

<400> SEQUENCE: 32

catggatcct ctatgtctct ttcac                                            25


<210> SEQ ID NO 33
<211> LENGTH: 22
<212> TYPE: DNA
<213> ORGANISM: Artificial Sequence
<220> FEATURE:
<223> OTHER INFORMATION: Synthesized

<400> SEQUENCE: 33

acaggatccg accttatctt ct                                               22


<210> SEQ ID NO 34
<211> LENGTH: 26
<212> TYPE: DNA
<213> ORGANISM: Artificial Sequence
<220> FEATURE:
<223> OTHER INFORMATION: Synthesized

<400> SEQUENCE: 34

accggatcct cttcttttca ttgttc                                           26


<210> SEQ ID NO 35
<211> LENGTH: 24
<212> TYPE: DNA
<213> ORGANISM: Artificial Sequence
<220> FEATURE:
<223> OTHER INFORMATION: Synthesized

<400> SEQUENCE: 35

tcaggatcct tttcttcgcc tggt                                             24


<210> SEQ ID NO 36
<211> LENGTH: 23
<212> TYPE: DNA
<213> ORGANISM: Artificial Sequence
<220> FEATURE:
<223> OTHER INFORMATION: Synthesized

<400> SEQUENCE: 36

ataggatcca tatgtgccgc ata                                              23


<210> SEQ ID NO 37
<211> LENGTH: 13
<212> TYPE: DNA
<213> ORGANISM: Artificial Sequence
<220> FEATURE:
<223> OTHER INFORMATION: Synthesized

<400> SEQUENCE: 37

tgaaaacaag aaa                                                         13
```

TRANSGENIC PLANT COMPRISING A CASSAVA VEIN MOSAIC VIRUS PROMOTER AND A HETEROLOGOUS NUCLEIC ACID SEQUENCE

TECHNICAL FIELD

This invention relates to compositions and methods useful in the production of transgenic plants. In particular, the invention relates to the plant virus (CsVMV) promoter sequences and to expression cassettes containing CsVMV promoter sequences. The invention also relates to vectors and transgenic plants containing CsVMV promoter sequences that are operably linked to heterologous DNA sequences. In addition, the invention relates to methods of producing transgenic plants by using vectors containing CsVMV promoter sequences.

BACKGROUND OF THE INVENTION

Isolated plant virus promoters are useful in the genetic engineering of plants to produce transgenic plants with desired phenotypic characteristics. In order to produce such transgenic plants, an isolated promoter is inserted into a vector and operably linked to a heterologous DNA sequence. Plant cells can then be transformed in a variety of ways by DNA constructs containing an isolated promoter fused to heterologous DNA sequences. The result of this transformation is that the promoter operably linked to the heterologous DNA is inserted into the genome of the transformed plant cell. Furthermore, the regulation of the expression of the heterologous DNA in the transformed plant cell is controlled by the promoter.

There are a variety of different approaches for producing a desired phenotype in a transgenic plant, depending on the nature of the heterologous sequences coupled to the isolated promoter. For example, expression of a novel gene that is not normally expressed in plant or in a particular tissue of a plant may confer a phenotypic change. Alternatively, the expression of a sense or an antisense construct introduced into transgenic plants can cause the inhibition of expression of endogenous plant genes. This inhibition of expression can, in turn, produce the desired phenotypic change.

There is a need for a variety of different promoters to be used in the genetic engineering of plants. These promoters are of several types. Constitutive promoters are one such commonly used type of promoter. Constitutive promoters are those which are capable of expressing operably linked DNA sequences in all tissues of a plant throughout normal development. In contrast to constitutive promoters, tissue-specific promoters are those promoters that are capable of selectively expressing heterologous DNA sequences in certain plant tissues. Promoters may also be inducible, e.g., by application of external inducing agents. Constitutive, inducible and tissue-specific promoters are used in the genetic engineering of plants, and have value for many different potential applications in this field.

Constitutive plant promoters may be obtained by isolating the regulatory region of a plant operon that is constitutively expressed. In addition to promoters obtained from plant genes, there are also promoters of bacterial and viral origin which have been used to constitutively express novel sequences in plant tissues. Examples of such promoters from bacteria include the octopine synthase (ocs) promoter, the nopaline synthase (nos) promoter and others derived from native Ti plasmids (see Herrera-Estrella et al, *Nature,* 303: 209-213, 1983). The 35S and 19S promoters of cauliflower mosaic virus are commonly used examples of viral promoters, (see Odel et al, *Nature,* 313:810-812, 1985).

In contrast to constitutive promoters, tissue-specific promoters are generally isolated from the promoter regions of plant genes that are selectively expressed in a specific plant tissue. These promoters can be fused with a heterologous DNA sequence and used to transform a plant cell to create transgenic plants that selectively express the heterologous DNA in a specific tissue. For example, the promoter regions from the fruit-specific, ethylene regulated genes E4 and E8 and from the fruit-specific polygalacturonase gene have been used to direct fruit specific expression of a heterologous DNA sequence in transgenic tomato plants. (See Cordes et al, *Plant Cell,* 1; 1025-1034, 1989; Deikman et al, *EMBO J.,* 7; 3315-3320, 1988; and Della Penna et al, *Proc. Natl. Acad. Sci. USA,* 83:6420-6424, 1986.)

Aspects of characterization, including genomic cloning, molecular characterization and sequencing, and description of the promoters, from several different plant viruses have been described, including cauliflower mosaic virus (CaMV), Hull, in "Virus Taxonomy", eds. Murphy et al., Wein, N.Y., Springer-Verlag, pp 189-192, 1995; commelina yellow mottle virus (ComYMV), Medberry et al, *Nuc. Acid Res.,* 18:5505-5513, 1990; rice tungo bacilliform virus (RTBV), Hay et al, *Nuc. Acids Res.,* 19:2615-2621, 1991; sugarcane bacilliform virus (ScBV), Bouhida et al, *J. Gen. Virol.,* 74:15-22, 1993; soybean chlorotic mottle virus (SbCMV) Hasegawa et al, *Nuc. Acids Res.,* 17:9993-10013, 1989; figwort mosaic virus (FMV), Richins et al, *Nuc. Acids Res.,* 15:8451-8466, 1987; carnation etch ringspot virus (CERV), Hull et al, *EMBO J.,* 5:3083-3090, 1986; peanut chlorotic streak virus (PCSV), Reddy et al, *Phytopathol.,* 83:129-133, 1993; strawberry vein banding virus (SVBV), GENBANK Accession No. X97304; and cacao swollen shoot virus (CSSV), GENBANK Accession No. L14546.

Cassava vein mosaic virus (previously referred to as CVMV, now referred to as CsVMV) was described by Calvert et al, *J. Gen. Virol.,* 76:1271-1276, 1995, and sequence data is also published as GENBANK Accession Nos. U59751 and U20341. In addition, the CsVMV promoter was recently described by Verdaguer et al, *Plant Mol. Biol.,* 31:1129-1139, 1996.

The discovery of both new constitutive promoters and new tissue-specific promoters is desired for the controlled expression of various nucleic acid sequences that are engineered into transgenic plants. There are many valuable potential applications of genetic engineering of plants. A variety of plant promoters with different characteristics and which are effective in different species of plants is desirable in order to bring these potential applications into practice.

BRIEF SUMMARY OF THE INVENTION

A promoter derived from CsVMV has now been cloned and molecularly characterized that can be used in a variety of transgenic plant cell types as a promoter for heterologous gene expression. The CsVMV promoter, and the derivative promoters described herein, provide a variety of advantages and benefits.

The promoters are shown to be active in both monocot and dicot plant species, and therefore can be readily applied to a variety of cultivated crops. Although generally constitutive, the derivative promoters described herein include promoters that can regulate expression in a tissue-specific manner, and therefore are useful for controlling expression of heterologous genes in a tissue-specific manner.

Thus in one embodiment the invention contemplates an isolated nucleic acid molecule comprising a promoter nucleotide sequence that is capable of initiating transcription of an operably linked heterologous nucleic acid sequence in a plant cell wherein the nucleotide sequence has at least 80% identity to 18 sequential nucleotides of the cassava vein mosaic virus (CsVMV) promoter shown in SEQ ID NO 3 (pA).

A preferred nucleic acid molecule comprises a nucleic acid sequence selected from the group consisting of CVP1, CVP2, pA, pB, pC, pD, pE, pΔB, pΔC, pΔD1, pΔD2, pΔD3, pΔDE1, pΔDE2, pΔDE3 and pΔE.

Also contemplated is a vector comprising a promoter nucleotide sequence of the invention that is operatively linked to a heterologous nucleic acid sequence. A chimeric gene comprising the promoter operatively linked to a heterologous nucleic acid sequence is also described.

The invention further contemplates a transgenic plant comprising a promoter nucleotide sequence of the invention that is operatively linked to a heterologous nucleic acid sequence.

The invention also describes a method of expressing a heterologous nucleic acid sequence in a plant cell comprising:

a) transforming a plant cell with a vector of the invention; and b) growing the plant cell under conditions where the heterologous nucleic acid sequence is expressed in the plant cell.

Other advantages and benefits will be readily apparent to one skilled in the art based on the disclosure herein

BRIEF DESCRIPTION OF THE DRAWINGS

In the drawings forming a portion of this disclosure:

FIG. 3 illustrates the nucleotide sequence of the CsVMV promoter region also shown in SEQ ID NO 3, including the CVP1 and CVP2 promoter fragments as described in Example 2. Using a transcription-based numbering system that is different from the genomic sequence numbering system, the transcription start site is designated +1. Consensus TATA box, as1 like sequence, Lam et al, *Proc Natl Acad of Sci USA,* 86:7890-7894, 1989, and the region homologous with the ComYMV promoter, Medberry et al, *Plant J,* 619-626, 1993, are boxed. AluI sites (arrows) indicate the 5' and 3' ends of the CVP1 promoter. Sequence motifs similar to previously characterized cis-elements in plant promoters are underlined (motifs with similarities with the box I element, Donald et al, *EMBO J,* 9:1717-1726, 1990, of the rbcS promoter, MNF1 binding site, Yanagisawa et al, *Plant Mol Biol,* 19:545-553, 1992, SV40 core enhancer, Ondek et al, *EMBO J,* 6:1017-1025, 1987, are indicated).

DETAILED DESCRIPTION OF THE INVENTION

A. Definitions

Figure 1:
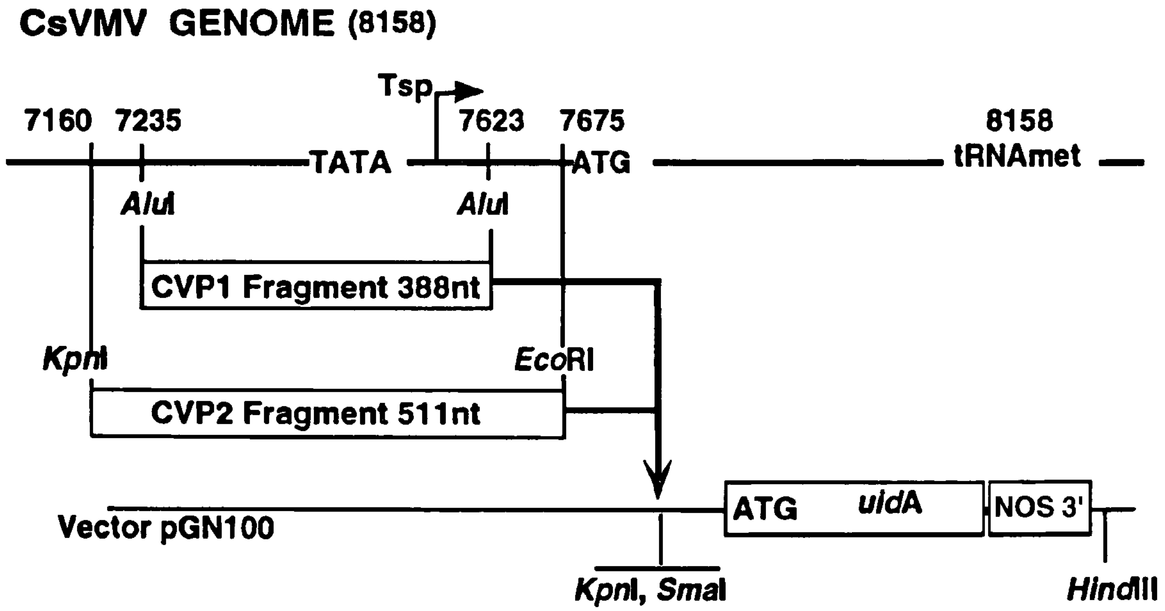
FIG. 1 illustrates a schematic diagraming the structure of a CsVMV promoter in the CsVMV viral genome and the construction of an uidA fusion gene containing either the CVP1 or CVP2 CsVMV promoter fragments as described in Example 1. Positions of the promoter fragments are numbered in the CsVMV genomic DNA. The CVP1 fragment was isolated using AluI restriction sites while the CVP2 fragment which included an additional 75 nucleotide at the 5' end and 52 nucleotides at the 3' end was obtained by PCR amplification using primers as described. The 3' end of CVP2 is just upstream of the first ATG codon in the viral genome. The transcription start site ("Tsp", right arrow) and the position of the consensus tRNA binding site ("tRNAmet") are also indicated. The schematic is not drawn to scale.

The term "nucleic acids", as used herein, refers to either DNA or RNA. "Nucleic acid sequence" or "polynucleotide sequence" refers to a single- or double-stranded polymer of deoxyribonucleotide or ribonucleotide bases read from the 5' to the 3' end. It includes self-replicating plasmids, infectious polymers of DNA or RNA and nonfunctional DNA or RNA. In the polynucleotide notation used herein, unless specified otherwise, the left hand end of single-stranded polynucleotide sequences is the 5' end; the left hand direction of double-stranded polynucleotide sequences is referred to as the 5' direction.

The term "promoter" refers to a region of DNA upstream from the translational start codon and which is involved in recognition and binding of RNA polymerase and other proteins to initiate transcription. A "plant promoter" is a promoter capable of initiating transcription in plant cells. The terms "CsVMV plant promoter" or "CsVMV promoter" as used herein refer to promoters derived from the promoter region of a CsVMV genome, and as further defined herein.

The terms "constitutive promoter or constitutive plant promoter" as used herein refer to a plant promoter which is capable of expressing operably linked DNA sequences in all tissues or nearly all tissues of a plant during normal development. The terms "inducible promoter" or "inducible plant promoter", as used herein, refer to plant promoters that are capable of selectively expressing operably linked DNA sequences at particular times or in particular tissues in response to endogenous or external stimuli.

The term "tissue-specific promoter" as used herein refers to promoters that are capable of selectively expressing operably linked DNA sequences in particular tissues. This means that the expression of the operatively linked DNA higher in one or several plant tissues than it is in the other tissues of the plant. For example, the CsVMV promoter present in the construct pΔDE1 is a tissue-specific promoter that selectively expresses operably linked heterologous DNA sequences in root tip tissue.

The term "operatively or operably linked" as used herein refers to linkage of the promoter 5' relative to the heterologous nucleic acid sequence such that the promoter mediates transcription of the linked DNA sequence. It is understood that the promoter sequence also includes transcribed sequences between the transcriptional start and the translational start codon.

The phrase "expression cassette", refers to nucleotide sequences which are capable of directing expression of a nucleic acid sequence or a structural gene in hosts compatible with such sequences. Such cassettes include at least promoters and transcription termination signals. Additional factors necessary or helpful in effecting expression may also be used as described herein.

The term "vector", refers to expression systems, nucleic acid-based shuttle vehicles, nucleic acid molecules adapted for nucleic acid delivery, and autonomous self-replicating circular DNA (e.g., plasmids, cosmids, phagemids and the like). Where a recombinant microorganism or cell culture is described as hosting an "expression vector," this includes extrachromosomal circular DNA (such as mitochondrial DNA or chloroplasts), DNA that has been incorporated into the host chromosome(s), or both. Where a vector is being maintained by a host cell, the vector can either be stably replicated by the cells during mitosis as an autonomous structure, incorporated within the host's genome, or maintained in the host's nucleus or cytoplasm.

The term "plasmid" refers to an autonomous circular DNA molecule capable of replication in a cell, and includes both the expression and nonexpression types. Where a recombinant microorganism or cell culture is described as hosting an "expression plasmid", this includes both extrachromosomal circular DNA molecules and DNA that has been incorporated into the host chromosome(s). Where a plasmid is being maintained by a host cell, the plasmid is either being stably replicated by the cells during mitosis as an autonomous structure or is incorporated within the host's genome.

A "heterologous sequence", a "heterologous DNA sequence", or a "heterologous nucleic acid sequence" as used herein, is one that originates from a foreign source (or species) or, if from the same source, is modified from its original form. Thus, a heterologous DNA encoding sequence operably linked to a promoter is from a source different from that from which the promoter was derived, or, if from the same source, is modified from its original form. Modification of the heterologous DNA sequence may occur, e.g., by treating the DNA with a restriction enzyme to generate a DNA fragment that is capable of being operably linked to the promoter. Modification can also occur by techniques such as site-directed mutagenesis.

The phrase "selectively hybridizing to" refers to a nucleic acid probe that hybridizes, duplexes or binds only to a particular target DNA or RNA sequence when the target sequences are present in a preparation or total cellular DNA or RNA. "Complementary" or "target" nucleic acid sequences refer to those nucleic acid sequences which selectively hybridize to a nucleic acid probe. Proper annealing conditions depend, for example, upon a probe's length, temperature, base composition, and the number of mismatches and their position on the probe, and must often be determined empirically. For discussions of nucleic acid probe design and annealing conditions, see, for example, Sambrook et al, Molecular Cloning: A Laboratory Manual (2nd ed.), Vols. 1-3, Cold Spring Harbor Laboratory, (1989) or Current Protocols in Molecular Biology, Ausubel et al, ed. Greene Publishing and Wiley-Interscience, New York (1987).

The phrase "nucleic acid sequence encoding" refers to a nucleic acid which codes for the expression of a specific protein, peptide or nucleic acid. The nucleic acid sequences include both the DNA strand sequence that is transcribed into RNA and the RNA sequence that is translated into protein. The nucleic acid sequences include both the full-length nucleic acid sequences as well as non full-length sequences derived from the full length sequence. It being further understood that the sequence includes the degenerate codons of the native sequence or sequences which may be introduced to provide codon preference in a specific host cell.

The term "isolated" when referring to nucleic acid sequences and molecules, refers to subject nucleic acids that do not contain the naturally occurring adjacent counterpart sequences, such as the CsVMV promoter in the context of the CsVMV genome, but rather are manipulated to be separated from other portions of the CsVMV genome, or to be recombined with heterologous sequences.

The phrase "substantially pure" when referring to nucleic acids indicates that the subject nucleic acid is purified from its biological source and is the predominant molecular species in the composition at hand, and preferably is at least 50% pure, and more preferably at least 90% pure nucleic acid as compared to other materials, such as protein, carbohydrate, lipids, and the like.

The term "plant" includes whole plants, plant organs (e.g., leaves, stems, roots, etc.), seeds and plant cells and progeny of same. The class of plants which can be used in the method of the invention is generally as broad as the class of higher plants amenable to transformation techniques, including both monocotyledonous (monocots) and dicotyledonous (dicots) plants. It includes plants of a variety of ploidy levels, including polyploid, diploid and haploid.

The term "transgenic plant" refers to a plant that has been produced by genetic engineering techniques. For example, plant cells transformed with vectors containing CsVMV promoters operably linked to heterologous DNA sequences can be used to produce transgenic plants with altered phenotypic characteristics.

The following terms are used to describe the sequence relationships between two or more nucleic acids or polynucleotides: "reference sequence", "comparison window", sequence identity", "percentage of sequence identity", and substantial identity". A "reference sequence" is a defined sequence used as a basis for a sequence comparison; a reference sequence may be a subset of a larger sequence, for example, as a segment of a full-length gene sequence given in a sequence listing, such as the nucleic acid sequence or may comprise a complete gene sequence.

Optimal alignment of sequences for aligning a comparison window may be conducted by the local homology algorithm of Smith et al, *Adv. Appl. Math.,* 2:482, 1981, by the homology alignment algorithm of Needleman et al, *J. Mol. Biol.,* 48:443, 1970, by the search for similarity method of Pearson et al, *Proc. Natl. Acad. Sci.* (*USA*), 85:2444, 1988, or by computerized implementations of these algorithms (GAP, BESTFIT, FASTA, and TFASTA in the Wisconsin Genetics Software Package Release 7.0, Genetics Computer Group, 575 Science Dr., Madison, Wis.). Other methods are described herein.

The terms "substantial identity" or "substantial sequence identity" as applied to nucleic acid sequences and as used herein denote a characteristic of a polynucleotide sequence, wherein the polynucleotide comprises a sequence that has at least 85 percent sequence identity, preferably at least 90 to 95 percent sequence identity, and more preferably at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the CsVMV promoter regions disclosed herein.

B. Cassava Vein Mosaic Virus (CsVMV) Promoters

This invention provides for CsVMV promoters and for DNA constructs containing a CsVMV promoter operably linked to a heterologous nucleic acid sequence. A CsVMV promoter is a promoter nucleotide sequence that is capable of initiating transcription of the heterologous nucleic acid sequence when present in a transcription medium capable of supporting transcription, such as in a plant cell, a plant or the like environment as described herein. The promoter initiates transcription of a heterologous nucleic acid operatively linked to the promoter.

As used herein, "CsVMV promoter" includes the wild-type CsVMV promoter identified herein, fragments thereof, such as the CVP1 and CVP2 fragments described herein, and derivatives thereof, such as the deletion constructs described herein, all which share the property of including nucleotide sequences derived from the sequence of the full-length CsVMV promoter described herein and shown in SEQ ID NO 3.

A preferred CsVMV promoter is a nucleotide sequence that has at least 80% identity to 18 sequential nucleotides of the CsVMV promoter shown in SEQ ID NO 3. Preferably, the identity is at least 90%, and more preferably is at least 98%. Preferably the identity is present in 20 sequential nucleotides, and more preferably in 25 sequential nucleotides. Percentage identity is a measure of the number of identical nucleotides in an uninterrupted linear (i.e., sequential) sequence of nucleotides when compared to a target nucleotide sequence of specified length.

As used herein, "identity" of a nucleotide sequence means that the compared nucleotide residues in two separate sequences are identical. Thus, 100% identity means, for example, that upon comparing 25 sequential nucleotides in two different molecules, both residues in all 25 pairs of compared nucleotides are identical.

A transcription medium can be any of a variety of environments, as is well known in the plant biotechnical arts, and therefore need not be limiting. However, exemplary and preferred mediums include a plant cell transformed by a nucleic acid comprising the subject promoter, such as a cultured plant cell, plant protoplasts, or other plant tissue culture configurations, non-differentiated plant cells, differentiated plant cells such as in cultured plantlets, transgenic plants, mature plants, and the like media. Also included are in vitro biochemical expression systems which comprise a reconstituted expression medium composed of purified proteins, substrates and components required to support transcription, as are known in the art.

A promoter of this invention can take the form of an isolated nucleic acid, a chimeric gene, an expression cassette, and the like recombinant DNA (rDNA) forms, as defined herein.

An isolated nucleic acid molecule comprises a promoter nucleotide sequence that contains a CsVMV promoter as described above.

A chimeric gene is a fusion comprising two different nucleotide sequences in which a subject promoter nucleotide sequence is operatively linked to a heterologous nucleic acid sequence such that, in an appropriate transcription medium, the heterologous nucleic acid is transcribed under the control of the subject promoter. Exemplary heterologous nucleic acid sequences for use in a chimeric gene can be any nucleic acid sequence that encodes a useful gene product. Useful gene products and heterologous nucleic acid sequences are described further herein.

Particularly useful are the various promoters described herein which allow control over the type of plant or plant tissue in which transcription will be promoted. For example, described herein are promoters which are constitutive for expression in a large variety of plant types, both monocot and dicot, including most tissues of the plant, and there are promoters described which preferentially limit transcription to certain tissues of the plant.

A preferred promoter nucleotide sequence comprises a nucleotide sequence that is derived from the CsVMV promoter shown in SEQ ID NO 3. "Derived from" in this context means the subject promoter was either made from, as by mechanical manipulation of the CsVMV promoter by deletions, fragmentation or substitution, or was designed from, as by analysis of the sequence and design and synthesis of a sequence, which derivative retains important, functional features of the CsVMV promoter as identified herein.

Preferably, promoter nucleotide sequence is one of the sequences described herein, i.e., any one of the promoter sequences present in the constructs named CVP1, CVP2, pA, pB, pC, pD, pE, pΔB, pΔC, pΔD1, pΔD2, pΔD3, pΔDE1, pΔDE2, pΔDE3 and pΔE. These preferred promoter nucleotide sequences are shown in the Sequence Listing herein as SEQ ID Nos 1, 2, 3, 4, 5, 6, 7, 9, 10, 11, 12, 13, 14, 15, 16 and 17, respectively.

CsVMV promoters are useful in the production of transgenic plants. Desired phenotypes are produced in transgenic plants as a result of transformation of plant cells by a DNA construct containing heterologous DNA sequence operably linked to a CsVMV promoter. A DNA construct therefore can comprise an expression cassette in any of a variety of expression vectors for use in a variety of plant cells.

There are a variety of methods known to those of skill in the art which may be used for preparation or isolation of CsVMV promoters. For example, CsVMV promoters can be isolated from genomic CsVMV DNA fragments.

CsVMV promoter sequences can also be isolated by screening plant cDNA libraries with oligonucleotide probes having sequences derived from the DNA sequence of the CsVMV promoter depicted herein. The various cloning methodologies described herein can also be used for the isolation of CsVMV promoters using the CsVMV promoter sequence of SEQ ID NO 3. Other methods known to those of skill in the art can also be used to isolate plant DNA fragments containing CsVMV promoters. See Sambrook, et al, for a description of other techniques for the isolation of DNAs related to DNA molecules of known sequence.

To prepare a cDNA library, mRNA is isolated from a tissue which expresses a target expressed gene to be cloned. For instance, the pericarp tissue of the fruit of a plant can be used. cDNA is prepared from the mRNA and then a second, complementary DNA strand is synthesized. Subsequently, this duplex DNA molecule is ligated into a recombinant vector. The vector is transfected into a recombinant host for propagation, screening and cloning. Methods for making and screening cDNA libraries are well known. See Gubler et al, *Gene,* 25:263-269, 1983 and Sambrook, et al.

For a genomic library, typically the DNA is extracted from plant tissue and either mechanically sheared or enzymatically digested to yield fragments of about 15-20 kb. The fragments are then separated by gradient centrifugation from undesired sizes and are constructed in bacteriophage lambda vectors. These vectors and phage are packaged in vitro, as described in Sambrook, et al. Recombinant phage are analyzed by plaque hybridization as described in Benton et al, *Science,* 196:180-182, 1977. Colony hybridization is carried out as generally described by Grunstein et al, *Proc. Natl. Acad. Sci. USA.,* 72:3961-3965, 1975. DNA of interest can be identified in either cDNA or genomic libraries by its ability to hybridize with nucleotide acid probes, for example on Southern blots, and these DNA regions are isolated by standard methods familiar to those of skill in the art. See Sambrook, et al.

Nucleic acid amplification techniques such as polymerase chain reaction (PCR) technology, can he used to amplify nucleic acid sequences from mRNA, from cDNA, and from genomic libraries or cDNA libraries. In PCR techniques, oligonucleotide primers complementary to the two 3' borders of the DNA region to be amplified are synthesized, the polymerase chain reaction is then carried out using the two primers. See PCR Protocols: A Guide to Methods and Applications (Innis et al, eds.), Academic Press, San Diego (1990). Primers can be selected to amplify the entire regions containing a desired promoter. PCR can also be used to amplify smaller DNA segments of these regions as desired.

PCR and related amplification techniques can be used in a number of ways to isolate DNA molecules that contain CsVMV promoters. For example, PCR can be used in a variety of protocols to isolate nucleic acids containing CsVMV promoters. In these protocols, appropriate primers and probes for amplifying DNA containing CsVMV promoters are generated from analysis of the DNA sequences listed herein.

Oligonucleotides for use in the disclosed procedures can be chemically synthesized according to the solid phase phosphoramidite triester method described by Beaucage et al, *Tetrahedron Lett.,* 22(20):1859-1862, 1981, using an automated synthesizer, as described in Needham-VanDevanter et al, *Nucl. Acids Res.,* 12:6159-6168, 1984. Purification of oligonucleotides is by either native acrylamide gel electrophoresis or by anion-exchange HPLC as described by Pearson et al, *J. Chrom.,* 255:137-149, 1983. The sequence of the synthetic oligonucleotide can be verified using the chemical degradation method of Maxam et al, *Meth. Enzymol.,* 65:499-560, 1980.

Different forms of a CsVMV promoter can be produced that have different properties as shown herein. A CsVMV promoter can be constructed in a variety of ways known to those of skill in the art. For example, promoters can be constructed by mapping restriction enzyme sites in the CsVMV promoter and then using the constructed map to determine appropriate restriction enzyme cleavage to excise a subset of the sequence. The shorter restriction fragment can then be inserted into a suitable vector. The construction of a specific promoter which controls expression of operably linked heterologous DNA sequences is shown herein. Other forms of promoter can also be prepared in a similar fashion.

Derivative forms of a promoter can be shown to express operably linked heterologous DNA sequences. This can be done by first preparing a vector that has an alternative form of the promoter operably linked to a reporter gene. Plant cells are then transformed with the vector and transgenic plants are produced from the transformed plant cells. Expression of the gene under the control of the promoter is then determined. See the Examples herein for a demonstration of the expression of a heterologous DNA sequence by an alternative form of a CsVMV promoter.

Alternatively, a nucleic acid molecule comprising a promoter of this invention can be synthesized by a variety of methods based on the sequence of a promoter described herein. Synthesis can be accomplished by chemical synthetic methods for the production of oligonucleotides as is described herein. In addition, a nucleic acid molecule can be prepared by the synthesis of a series of oligonucleotides which correspond in sequence with different portions of the promoter, and which can be combined by ligation to form larger nucleic acid molecules.

C. Vectors for Expressing Heterologous Proteins

The different forms of a CsVMV promoter described herein can be used in expression cassettes, vectors and other DNA constructs.

A vector of this invention is a nucleic acid molecule that comprises a promoter nucleotide sequence according to the present invention that is operatively linked to a heterologous nucleic acid sequence. Typically, the vector is capable of expressing the operatively linked promoter and heterologous nucleic acid sequences as a chimeric gene. Vectors suitable for use in expressing chimeric genes are generally well known, and need not be limited.

A chimeric gene for use in a vector herein is a fusion between a promoter nucleotide sequence of this invention operatively linked to a heterologous nucleic acid sequence. Any of a variety of heterologous nucleic acid sequences can be used in a chimeric gene capable of altering a plant phenotype and can include plant, animal or other organismal proteins or nucleic acids. Exemplary proteins include agriculturally useful proteins for increasing plant production, disease resistance, capabilities to utilize modified nutrients, and the like proteins.

For example, the CsVMV promoter can be used operably linked to, e.g., genes for herbicide resistance; genes for fungal disease resistance (e.g., chitinases and glucanases); genes for bacterial disease resistance (e.g., cecropins); and genes for insect resistance (e.g., *B. thuringiensis* toxin). Additional examples include viral coat proteins such as the coat protein of CsVMV or the replicase of african cassava mosaic virus.

The CsVMV promoter can also be used operably linked to, e.g., genes for ripening or degradation (e.g., Acc oxidase, Acc synthase, polygalacturonase, phytoene synthase); genes for color; genes for sweetness, and the like genes.

Expression cassettes containing a CsVMV promoter can be constructed in a variety of ways. These techniques are known to those of skill in the art and are described generally in Sambrook, et al., supra. For instance, various procedures, such as site directed mutagenesis can be used to introduce a restriction site at the start codon of a heterologous gene fragment. Heterologous DNA sequences are then linked to the CsVMV promoter such that the expression of the heterologous sequences is regulated by the promoter. DNA constructs composed of a CsVMV promoter operably linked to heterologous DNA sequences can then be inserted into a variety of vectors. Such vectors include expression vectors that are useful in the transformation of plant Cells. Many other such vectors useful in the transformation of plant cells can be constructed by the use of recombinant DNA techniques well known to those of skill in the art.

Exemplary vectors for expression in protoplasts or plant tissues include pUC 18/19 or pUC 118/119 (GIBCO BRL, Inc., MD); pBluescript SK (+/−) and pBluescript KS (+/−) (STRATAGENE, La Jolla, Calif.); pT7Blue T-vector (NOVAGEN, Inc., WI); pGEM-3Z/4Z (PROMEGA Inc., Madison, Wis.), and the like vectors, such as is described herein.

Exemplary vectors for expression using *Agrobacterium tumefaciens*-mediated plant transformation include pBin 19 (CLONETECH), Frisch et al, *Plant Mol. Biol.,* 27:405-409, 1995; pCAMBIA 1200 and pCAMBIA 1201 (Center for the Application of Molecular Biology to International Agriculture, Canberra, Australia); pGA482, An et al, *EMBO J.,* 4:277-284, 1985; pCGN1547, (CALGENE Inc.) McBride et al, *Plant Mol. Biol.,* 14:269-276, 1990, and the like vectors, such as is described herein.

Techniques for nucleic acid manipulation of genes such as subcloning a subject promoter or heterologous nucleic acid sequences into expression vectors, labeling probes, DNA hybridization, and the like are described generally in Sambrook, et al., Molecular Cloning—A Laboratory Manual (2nd Ed.), Vol. 1-3, Cold Spring Harbor Laboratory, Cold Spring Harbor, N.Y., 1989, which is incorporated herein by reference. This manual is referred to herein as "Sambrook, et al.".

D. Transgenic Plants

The invention also contemplates a transgenic plant comprising a promoter of the present invention in a chimeric gene construct as described herein. The plant has an altered phenotype due to the expression of the heterologous nucleic acid sequence which is expressed under the control of the subject promoter. The transgenic plant therefore contains an expression cassette as defined herein as a part of the plant, the cassette having been introduced by transformation of a plant with a vector of this invention.

Because the promoters of the present invention can function is a wide variety of plants, including monocots and dicots, a transgenic plant can be any type of plant which contains a subject promoter and which can express the heterologous nucleic acid sequence in a chimeric gene containing the promoter. Exemplary plant species and genuses are described further herein.

Techniques for transforming a wide variety of plant species are well known and described in the technical and scientific literature. See, for example, Weising et al, *Ann. Rev. Genet.,* 22:421-477, 1988. As described herein, a constitutive or inducible CsVMV promoter is operably linked to the desired heterologous DNA sequence in a suitable vector. The vector comprising a CsVMV promoter fused to heterologous DNA will typically contain a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorsulfuron or Basta. Such selective marker genes are useful in protocols for the production of transgenic plants.

DNA constructs containing a CsVMV promoter linked to heterologous DNA can be introduced into the genome of the desired plant host by a variety of conventional techniques. For example, the DNA construct may be introduced directly into the DNA of the plant cell using techniques such as electroporation and microinjection of plant cell protoplasts. Alternatively, the DNA constructs can be introduced directly to plant tissue using biolistic methods, such as DNA micro-particle bombardment. In addition, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski et al, *EMBO J.,* 3:2717-2722, 1984. Electroporation techniques are described in Fromm et al, *Proc. Natl. Acad. Sci. USA,* 82:5824, 1985. Biolistic transformation techniques are described in Klein et al, *Nature* 327:70-73, 1987. The full disclosures of all references cited are incorporated herein by reference.

A variation involves high velocity biolistic penetration by small particles with the nucleic acid either within the matrix of small beads or particles, or on the surface (Klein et al, *Nature,* 327:70-73, 1987). Although typically only a single introduction of a new nucleic acid segment is required, this method particularly provides for multiple introductions.

*Agrobacterium tumefaciens*-meditated transformation techniques are well described in the scientific literature. See, for example Horsch et al, *Science,* 233:496-498, 1984, and Fraley et al, *Proc. Natl. Acad. Sci. USA,* 90:4803, 1983. See the Examples herein for a demonstration of the transformation of plant cells with a vector comprising a CsVMV promoter by *Agrobacterium tumefaciens.*

More specifically, a plant cell, an explant, a meristem or a seed is infected with *Agrobacterium tumefaciens* transformed with the segment. Under appropriate conditions known in the art, the transformed plant cells are grown to form shoots, roots, and develop further into plants. The nucleic acid segments can be introduced into appropriate plant cells, for example, by means of the Ti plasmid of *Agrobacterium tumefaciens*. The Ti plasmid is transmitted to plant cells upon infection by *Agrobacterium tumefaciens*, and is stably integrated into the plant genome (Horsch et al, *Science,* 233:496-498, 1984; Fraley et al, *Proc. Nat'l. Acad. Sci. U.S.A.,* 80:4803, 1983.

Ti plasmids contain two regions essential for the production of transformed cells. One of these, named transfer DNA (T DNA), induces tumor formation. The other, termed virulent region, is essential for the introduction of the T DNA into plants. The transfer DNA region, which transfers to the plant genome, can be increased in size by the insertion of the foreign nucleic acid sequence without its transferring ability being affected. By removing the tumor-causing genes so that they no longer interfere, the modified Ti plasmid can then be used as a vector for the transfer of the gene constructs of the invention into an appropriate plant cell, such being a "disabled Ti vector".

All plant cells which can be transformed by *Agrobacterium* and whole plants regenerated from the transformed cells can also be transformed according to the invention so as to produce transformed whole plants which contain the transferred foreign nucleic acid sequence.

There are various ways to transform plant cells with *Agrobacterium*, including:

(1) co-cultivation of *Agrobacterium* with cultured isolated protoplasts, (2) co-cultivation of cells or tissues with *Agrobacterium*, or (3) transformation of seeds, apices or meristems with *Agrobacterium.*

Method (1) requires an established culture system that allows culturing protoplasts and plant regeneration from cultured protoplasts.

Method (2) requires (a) that the plant cells or tissues can be transformed by *Agrobacterium* and (b) that the transformed cells or tissues can be induced to regenerate into whole plants.

Method (3) requires micropropagation.

In the binary system, to have infection, two plasmids are needed: a T-DNA containing plasmid and a vir plasmid. Any one of a number of T-DNA containing plasmids can be used, the only requirement is that one be able to select independently for each of the two plasmids.

After transformation of the plant cell or plant, those plant cells or plants transformed by the Ti plasmid so that the desired DNA segment is integrated can be selected by an appropriate phenotypic marker. These phenotypic markers include, but are not limited to, antibiotic resistance, herbicide resistance or visual observation. Other phenotypic markers are known in the art and may be used in this invention.

The present invention embraces use of the claimed promoters in transformation of any plant, including both dicots and monocots. Transformation of dicots is described in references above. Transformation of monocots is known using various techniques including electroporation (e.g., Shimamoto et al, *Nature,* 338:274-276, 1992; ballistics (e.g., European Patent Application 270,356); and *Agrobacterium* (e.g., Bytebier et al, *Proc. Nat'l Acad. Sci. USA,* 84:5345-5349, 1987).

Transformed plant cells which are derived by any of the above transformation techniques can be cultured to regenerate a whole plant which possesses the desired transformed phenotype. Such regeneration techniques rely on manipulation of certain phytohormones in a tissue culture growth medium typically relying on a biocide and/or herbicide marker which has been introduced together with the nucleotide sequences. Plant regeneration from cultured protoplasts is described in Evans et al, Handbook of Plant Cell Culture, pp. 124-176, MacMillan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally by Klee et al, *Ann. Rev. Plant Phys.,* 38:467-486, 1987.

Additional methods for producing a transgenic plant useful in the present invention are described in U.S. Pat. Nos. 5,188,642; 5,202,422; 5,463,175; and 5,639,947, the disclosures of which are hereby incorporated by reference.

One of skill will recognize that, after an expression cassette comprising the CsVMV promoter is stably incorporated in transgenic plants and confirmed to be operable, it can be introduced into other plants by sexual crossing. Any of a number of standard breeding techniques can be used, depending upon the species to be crossed.

The methods and compositions of the invention have use over a broad range of types of plants, including species from the genera *Fragaria, Lotus, Medicago, Onobrychis, Trifolium, Trigonella, Vigna, Citrus, Linum, Geranium, Manihot, Daucus, Arabidopis, Brassica, Raphanus, Sinapis, Atropa, Capsicum, Hyoscyamus, Lycopersicon, Nicotiana, Solanum, Petunia, Digitalis, Majorana, Ciohorium, Helianthus, Lactuca, Bromus, Asparagus, Antirrhinum, Herecocallis, Nemesia, Pelargonium, Panicum, Pennisetum, Ranuncultis, Senecio, Salpiglossis, Cucumis, Browaalia, Glycine, Lolium, Zea, Triticum, Sorghum, Datura, Chrysanthemum, Dianthus, Gerbera, Euphorbia, Ipomoea, Passiflora, Cyclamen, Malus, Prunus, Rosa, Rubus, Populus, Santalum, Allium, Lilium, Narcissus, Ananas, Arachis, Phaseolus* and *Pisum*, and more particularly including oil crops such as canola (*Brassica* sp.), cotton (*Gossypium* sp.), peanut (*Arachis* sp.), sunflower (*Helianthus* sp.), palm (*Elaeis* sp.), flax (*Linum* sp.), safflower (*Carthamus* sp.), coconut (*Cocos* ap.) and soybean (*Glycine* sp.); grain crops such as wheat (*Triticum* sp.), corn (*Zea* sp.), sorghum (*Sorghum* sp.), barley (*Hordeum* sp.), rye (*Secale* sp.), oats (*Averia* sp.) and rice (*Oryza* sp.); fruit crops such as banana (*Musa* sp.), citrus (*Citrus* sp.), berries (e.g., strawberry (*Fragaria* Sp.) or raspberry (*Rubus* sp.) mango (*Mangifera* sp.), melon (*Cucumis* sp.), pear (*Pyrus* sp.), cucumber (*Cucumis* sp.), and apricot, peach, cherry, plum and prune (*Prunus* sp.); vegetable crops such as pea (*Pisum* sp.), bean (*Vicia* sp.), broccoli and related crucifers (*Brassica* sp.), spinach (*spinacia* sp.), onion (*Allium* sp.), celery (*Apiurti* sp.), carrot (*Daucus* sl).), asparagus (*Asparagus* sp.), and artichoke (*Helianthus* sp.); tomato (*Lycopersicon esculenium*), pepper (*Capsicum annuum*); additional ornamental crops such as tulip (*Tulipa* sp.), snapdragon (*Antirrhinum* sp.), Iris (*Iris* sp.), Orchids (*Cymbidium* and *Cattleya* sp.), pelargonium; beverage crops such as coffee (*Coffea* sp.) and tea (*Thea* sp.); herb crops such as mint (*Mentha* sp.), thyme (*Thymus* sp.) marjoram (*Origanum* sp.), okra, coffee, potato, tubers, taro.

E. Methods for Expressing Heterologous Nucleic Acids in Plants

DNA constructs, chimeric genes and expression cassettes containing CsVMV promoters of this invention can be used to transform plant cells and produce transgenic plants with desired phenotypic characteristics. There are a variety of different approaches one can use to produce a desired phenotype in transgenic plants. For example, by using methods described herein, one can operatively link a novel gene to a CsVMV promoter and transform plant cells. Transgenic plants can be produced from the transformed plant cells so that the novel gene product is produced in all tissues or in only certain tissues of a transgenic plant. In this context, the term "novel gene" refers to a gene that is not normally present in a plant or which, if present, is not normally expressed in a particular plant cell tissue. The expression of the novel gene can result in the production of a protein that confers an altered phenotype for a transgenic plant.

Thus, the invention contemplates a method for expressing a heterologous nucleic acid sequence in a plant cell comprising:

a) transforming the plant cell with a vector comprising a promoter nucleotide sequence according to the present invention that is operatively linked to the heterologous nucleic acid sequence; and b) growing the plant cell under conditions where the heterologous nucleic acid sequence is expressed in the plant cell.

Methods for transforming a plant cell can vary widely and need not be so limited. Exemplary transformation methods are described herein.

The method for expression can include objectives such as to provide a heterologous protein that confers a desirable phenotype upon expression and transcription of the heterologous nucleic acid sequence, to provide an expressed nucleic acid which can function as an anti-sense molecule, to provide an expressed nucleic acid which can regulate gene expression or processing of nucleic acids, and the like objectives within a transgenic plant.

DNA constructs containing a CsVMV promoter operably linked to a heterologous DNA sequence can therefore be used in a number of techniques to suppress expression of endogenous plant genes, e.g., sense or antisense suppression. In antisense technology, a nucleic acid segment from the desired plant gene is cloned and operably linked to a CsVMV promoter such that the anti-sense strand of RNA will be synthesized. The construct is then transformed into plants and the antisense strand of RNA is produced. In plant cells, it has been shown that anti-sense RNA inhibits gene expression; see, e.g., Sheehy et al, *Proc. Nat. Acad. Sci. USA,* 85:8805-8809, 1988, and Hiatt et al., U.S. Pat. No. 4,801,340 which are incorporated herein by reference.

The nucleic acid segment to be introduced in antisense suppression generally will be substantially identical to at least a portion of the endogenous gene or genes, function or functions, to be repressed, but need not be identical. The vectors of the present invention can be designed such that the inhibitory effect applies to other proteins within a family of genes exhibiting homology or substantial homology to the target gene. Segments from a gene can be used (1) directly to inhibit expression of homologous genes in different plant species, or (2) as a means to obtain the corresponding sequences, which can be used to suppress the gene.

The introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments will be equally effective. Normally, a sequence of between about 30 or 40 nucleotides and about 2,000 nucleotides should be used, though a sequence of at least about 100 nucleotides is preferred, a sequence of at least about 200 nucleotides is more preferred, and a sequence of at least about 500 nucleotides is especially preferred.

Catalytic RNA molecules or ribozymes also have been reported to have use as a means to inhibit expression of endogenous plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon then, thereby increasing the activity of the constructs.

A number of cases of ribozymes have been identified. One class of ribozyme is derived from a number of small circular RNAs which are capable of self-cleavage and replication in plants. The RNAs replicate either alone (viroid RNAS) or with a helper virus (satellite RNAS). Examples include RNAs from avocado sunblotch viroid and the satellite RNAs from tobacco ringspot virus, lucerne transient streak virus, velvet tobacco mottle virus, *solanum nodiflorum* mottle virus and subterranean clover mottle virus. The design and use of target RNA-specific ribozymes is described in Haseloff et al, *Nature,* 334:585-591, 1988.

A preferred method of suppression is sense suppression. Introduction of a nucleic acid configured in the sense orientation has been shown to be an effective means by which to block the transcription of target genes. For examples of the use of this method to modulate expression of endogenous genes see, Napoli et al, *The Plant Cell,* 2:279-289, 1990, and U.S. Pat. No. 5,034,323. Sense suppression is a preferred method for ripening control (e.g., Acc oxidase or Acc synthase), sweetness control (e.g., ADPG pyrophosphorylase), or color modification (e.g., chalcone synthase); see U.S. Pat. No. 5,034,323.

Generally, in sense suppression, transcription of the introduced sequence occurs. The effect may also occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity is useful to exert a more effective repression of expression of the endogenous sequences. Substantially greater identity of more than about 80% is preferred, although about 95% to absolute identity would be most preferred. The effect may be applied to other proteins within a similar family of genes exhibiting homology or substantial homology. Segments from a gene can be used (1) directly to inhibit expression of homologous genes in different plant species, or (2) as a means to obtain the corresponding sequences, which can be used to suppress the gene.

In sense suppression, the introduced sequence, needing less than absolute identity, also need not be full length, relative to either the primary transcription product or fully processed mRNA. A higher identity in a shorter than full length sequence compensates for a longer, less identical sequence. Furthermore, the introduced sequence need not have the same intron or exon pattern, and identity of non-coding segments may be equally effective. A sequence of a size of at least 50 base pairs is preferred, with greater length sequences being more preferred; see U.S. Pat. No. 5,034,323.

The expression of the heterologous DNA sequences linked to a CsVMV promoter can be detected in a variety of ways, depending on the nature of heterologous sequences. For example, one may assay for the desired phenotype. The desired phenotype which results from the successful expression of heterologous DNA sequences under control of a CsVMV promoter may be determined by a variety of ways, depending on the phenotypic trait that is introduced. For instance, resistance to a herbicide can be detected by treatment with the herbicide.

Expression of the heterologous DNA can also be detected by measurement of the specific RNA transcription product. This can be done by, for example, RNAse protection or Northern blot procedures. If heterologous DNA sequences encode a novel protein, the protein product may be assayed, for instance, by its function or by a variety of immunoassay techniques. For example, a novel protein product with enzymatic activity can be measured in an enzyme assay.

EXAMPLES

The following examples are provided by way of illustration and not limitation.

1. Isolation of a Cassava Vein Mosaic Virus (CsVMV) Promoter

Molecular techniques were carried out essentially as described by Sambrook et al, *Molecular Cloning: A Laboratory Manual*, Cold Spring Harbor Laboratory Press, Cold Spring Harbor, N.Y., 1989.

Nucleotide numbers refer to the cassava vein mosaic virus genome nucleotide sequence reported by Calvert et al, *J Gen Virol,* 76:1271-1276, 1995, and as published with GENBANK Accession Nos. U59751 and U20341. GENBANK is a nucleotide sequence database provided by National Medical Library at the National Center for Biotechnology Information at the National Institutes of Health, Bethesda, Md. The original CsVMV full length genomic clone was provided by Dr. R. Shepherd (University of Kentucky). The clone was constructed by ligating the full length CsVMV viral genomic DNA cut at a unique BglII site in the BglII site of the plasmid pCKIZ, Anza, O., *Replication and mapping of caulimoviruses*, PhD thesis, University of California, David, USA, 1982. Six overlapping fragments were isolated using convenient restriction sites and each fragment was cloned in plasmid pUC119. Automatic sequencing, using an Applied Biosystems model 373A sequencing apparatus, was carried out by Taq-mediated elongation using dye-labeled primers. When necessary, PCR reactions were performed and direct sequencing of the PCR product was carried out. Sequence data was compiled using the SeqEd software provided by the manufacturer of the automated sequencer.

Restriction fragments derived directly from the genomic clone were cloned into pUC119 plasmid. Using these subclones, two viral DNA fragments containing a consensus TATA box motif were isolated (FIG. 1). A fragment designated CVP1 encompassed CsVMV nucleotides 7235 to 7623 and was obtained by AluI enzymatic digestion. A larger fragment containing CsVMV nucleotides 7160 to 7675 and designated CVP2, was isolated by PCR amplification. The two oligonucleotides used in the PCR reaction were: primer 1, 5'ACCGGTACCAGAAGGTAATTATCCAAGATGT3' (SEQ ID NO 18) (CsVMV sequence from nucleotide 7160 to 7183 with the addition of a KpnI restriction site at the 5' end) and primer 2, 5'CGGAATTCAAACTTACAAATTTCTCTGAAG3' (SEQ ID NO 19) (CsVMV sequence complementary to nucleotides 7652 to 7675 with the addition of an EcoRI restriction site at the 5' end). The amplification reaction contained 25 pmol of each primer, 200 μM each dNTP, 100 ng of plasmid DNA containing the sequence to be amplified, 2.5 U Pfu polymerase and the appropriate buffer (STRATAGENE). Initial denaturation was performed at 94° C. for 5 min then the reaction mixture was denatured at 94° C. for 1 min, annealed at 60° C. for 1 min and elongated at 72° C. for 1 min for each of 15 cycles. Final extension was carried out for 5 min at 72° C. Sequence accuracy of the amplification product was subsequently confirmed by dideoxynucleotide chain-termination sequencing (SEQUENASE USB).

The chimeric plasmids pILTAB:CVP1 and pILTAB:CVP2 (FIG. 1) were used to study promoter activity and were prepared as described below. CVP1 and CVP2 promoters fragments were respectively ligated into SmaI and EcoRI/KpnI sites of pGN100, a pUC 119 derived plasmid containing the uidA coding sequence linked to the 3' polyadenylation signal of the nopaline synthase gene (nos 3') as illustrated in FIG. 1.

The cassettes containing the CsVMV promoter:uidA fusion genes were excised by KpnI/HindIII digestion from pILTAB:CVP1 and pILTAB:CVP2 and subcloned at KpnI/HindIII sites in the pBIN19 binary vector (CLONETECH) used for *Agrobacterium*-mediated plant transformation. The plasmid pe35GN contains the enhanced 35S promoter, Kay et al, *Science,* 236:1299-1302, 1987, and the uidA coding sequence linked to the nos 3' end. The plasmid pDO432 contains the luciferase coding sequence from *Photinus pyralis* under the control of the 35S promoter, Ow et al, *Science,* 234:856-859, 1986. Plasmids pILTAB:CVP1, pILTAB:CVP1 and pe35GN used in transient assay experiments are each approximately 5.5 kb in size.

2. Transcription Start Site for CsVMV Promoter

The transcription start site of the CsVMV promoter was determined by primer extension analysis using total RNA recovered from transgenic tobacco plants which harbor the CVP1:uidA fusion gene prepared as described in Example 4.

Total RNA was extracted from young leaves of transgenic tobacco plants as described by Prescott and Martin, *Plant Mol Biol Reporter,* 4:219-224, 1987, with minor modifications. Primer extension was performed with a 34 bp long oligonucleotide with the sequence 5'-CGCGATCCAGACTGAATGCCCACAGGCCGTCGAG-3' (SEQ ID NO 20) which is complementary to a region 34 nucleotides downstream of the ATG start codon in the uidA gene. The oligonucleotide (20 pmol) was 5' end labeled using 6 U of T4 polynucleotide kinase (USB) and 7 μCi of [γ-32P]ATP (3000 μCi/mmol, 10 μCi/μl). After the labeling reaction the primer was purified using Nuctrap Push columns (STRATAGENE). One-tenth pmol of the labeled primer was mixed with 50 μg of total RNA from transgenic plants. The experiment was performed according to Sambrook et al, *Molecular cloning: A laboratory manual*, Cold Spring Harbor Laboratory Press, Cold Spring Harbor, N.Y., 1989, except that annealing was carried out at 30° C. or 40° C. for 12 hours, and the extension reaction was allowed to proceed for 1 hour at 42° C. with 20 U of AMV reverse transcriptase (GIBCOBRL) The extension products were separated on a 7.5% polyacrylamide gel containing 7M urea. Sequence reactions (SEQUENASE USB) performed with the same labeled primer were subjected to electrophoresis in adjacent lanes on the same gel.

Figure 2:
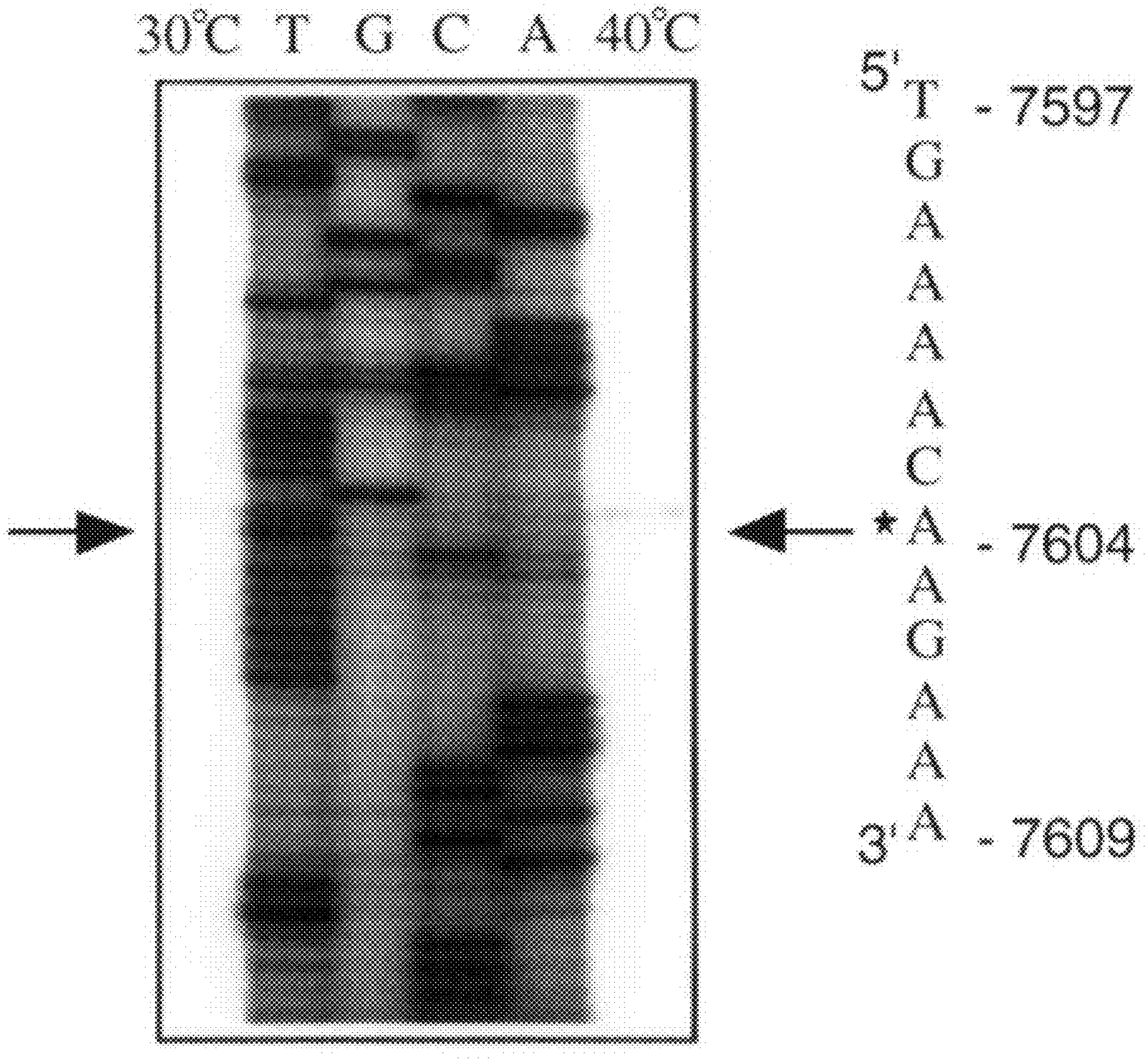
FIG. 2 illustrates the determination of the transcription start site of the CsVMV promoter as described in Example 2. Primer extension reactions were carried out as described and the products of the extension reactions obtained with two annealing temperature (30° C. and 40° C.) and reference sequencing reactions of CVP1-uidA gene construct (lane A, C, G and T) performed with the same labeled primer, were subjected to electrophoresis in a 7M urea, 7.5% polyacrylamide gel. The plus strand DNA sequence (complementary to the sequence read on the gel) is shown (SEQ ID NO: 37) and the transcription start site (A*) is indicated by an arrow at nucleotide number (nt.) 7604. Numbers correspond to the nucleotide sequence numbers of the CsVMV genome, Calvert et al, *J Gen Virol,* 76:1271-1276, 1995.

A single major extension product was detected and mapped to an adenine residue (nt. 7604) located 35 nucleotides downstream of the putative TATA box (FIG. 2). By comparison with the location of the start of transcription reported for other plant pararetrovirus promoters (Guilley et al, *Cell,* 30:763-773, 1982; Hay et al, *Nucl Acids Res,* 19:2615-2621, 1991; Medberry et al, *Nucl Acids Res,* 18:5505-5513, 1990; and Sanfa on, H., *Virology,* 198:39-49, 1994) the transcription start site reported here at nt. 7604 represents the 5' end of the CsVMV transcript. By comparing sequence of the CsVMV promoter from the TATA box to the start of transcription with those of caulimovirus promoters FMV 34S and CaMV 35S (Gardner et al, *Nucl Acids Res,* 9:2871-2887, 1981. 17; and Richins et al, *Nucl Acids Res* 15:8451-8466, 1987) we concluded that these three promoters are, in this region, closely related to each other. In contrast there is less homology with the promoters from badnaviruses (ComYMV and RTBV).

The nucleotide sequence of the promoter region of a CsVMV genome is presented in FIG. 3 and was confirmed by the results reported by Calvert et al, *J Gen Virol,* 76:1271-1276, 1995. The numbering system shown in FIG. 3 is based on the transcription start site where +1 corresponds to the transcription start site reported herein as nt. 7604 using the genomic sequence numbers. Thus, CVP1 comprises 387 nucleotides from position −368 to +20 and CVP2 comprises a fragment of 514 nucleotides from position −443 to +72 (FIG. 3).

A comparison of the CsVMV promoter sequence with pararetrovirus promoter sequences, namely the 35S CaMV, Gardner et al, *Nucl Acids Res,* 9:2871-2887, 1981, the 34S FMV, Richins et al, *Nucl Acids Res* 15:8451-8466, 1987, RTBV, Qu et al, *Virology,* 185:354-364, 1991, and ComYMV, Medberry et al, *Nucl Acids Res,* 18:5505-5513, 1990, promoters revealed the presence of a conserved TATA box as mentioned previously, and a 17 nucleotides motif AGACGTAAGCACTGACG (position −203 to −219) (SEQ ID NO 21) that has strong homology with the transcriptional enhancer as1 found in the 35S CaMV, FMV and ComYMV promoters. A 22 nucleotides sequence CTTATCACAAAGGAATCTTATC (position −90 to −111) (SEQ ID NO 22) was also identified that is present in the ComYMV promoter but not in RTBV or caulimovirus promoters. This limited homology indicated that we had isolated a distinct plant pararetrovirus promoter.

In addition, recent developments in the field of virus taxonomy have recognized the differences between the cauliflower mosaic virus (CaMV) and the cassava vein mosaic virus (CsVMV) to the extent that a new genus has been adopted for CsVMV. Specifically, the International Committee on Taxonomy of Viruses (ICTV) has met in May, 1997, and adopted a change in viral nomenclature such that CsVMV is in the genus "cassemovirus" and CaMV is in the genus caulimovirus.

Figure 4:
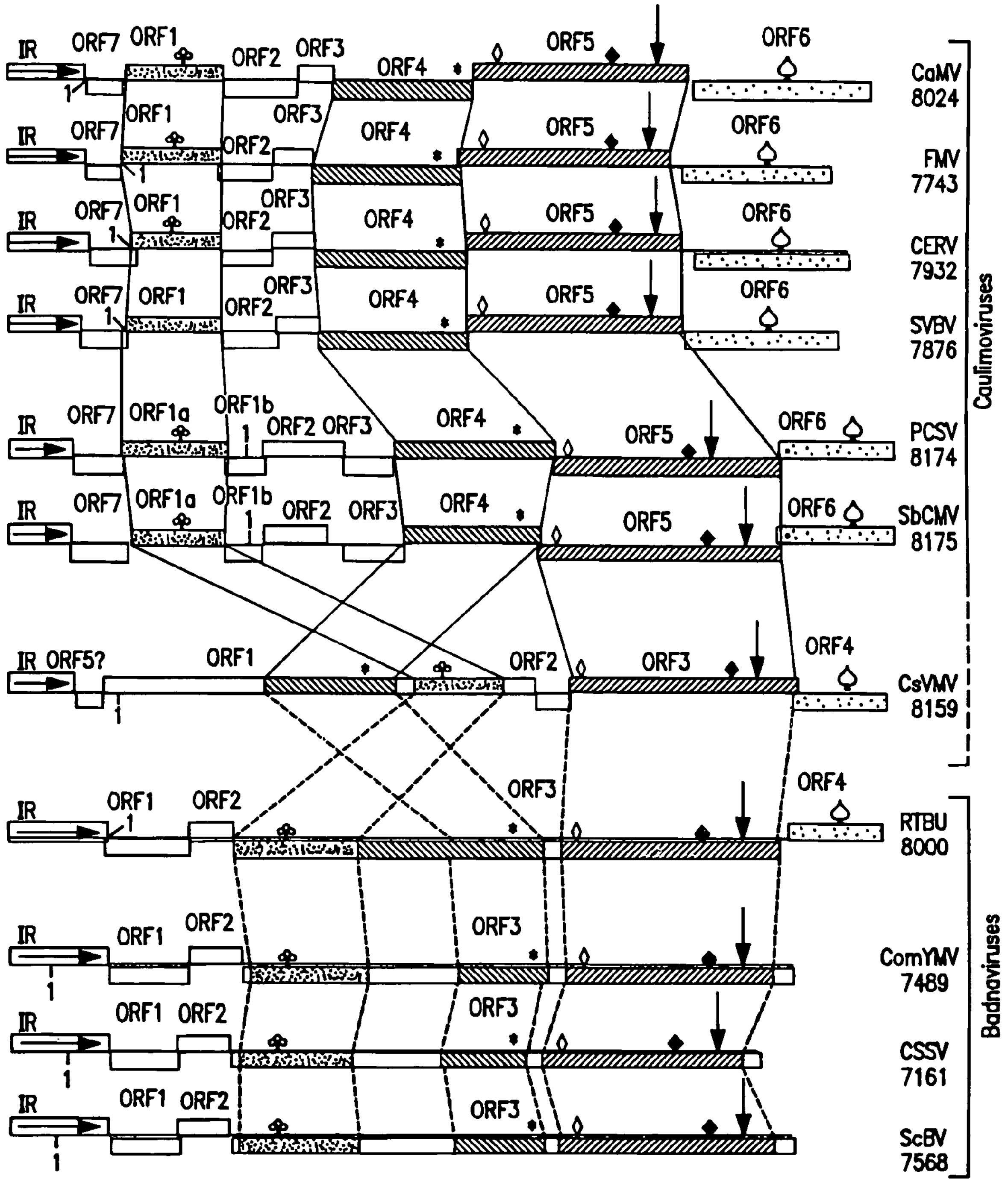
FIG. 4 illustrates the comparison of the genomic organization of CsVMV with viral genomes of caulimoviruses and badnaviruses as described in Example 2. All the maps start at the beginning of the intergenic region. ORFs or ORF segments encoding similar putative functions are linked by vertical lines. The numeral "1" indicates the origin of DNA replication. ♣: MP active site; ♦: RT active site; ♠: TAV active center; ✻: RNA binding site; ◇: PR active site; ⇓: RNAse H consensus sequence.

The basis for the change is summarized in FIG. 4 which illustrates a comparison of the genomic organization of a variety of related viruses. In particular, it is noted that the order of two of the major proteins (coat protein and movement protein) is reversed on the genome relative to CaMV, and that these two proteins are encoded for by a single ORF that is processed as a polyprotein whereas on CaMV these two proteins are encoded by two separate ORFs designated ORF1 and ORF4, and the actual nucleotide sequence of many of the ORFs are substantially different from CaMV.

The viral sequences were analyzed using programs from the DNASTAR package for Macintosh (DNASTAR Inc., Madison, Wis.). The published sequences were obtained from GENBANK using the following publication numbers (in parenthesis) for each viral strain: CaMV Strasbourg strain (J02048), CERV (X04658), FMV (X06166), SVBV (X97304), PCSV (U13988), SbCMV (.times.15828), RTBV (M65026), ComYMV (X52938), CSSV (L14546), ScBV (M89923).

Regarding degrees of homology between CaMV and CsVMV, it is noted that there is about 23% homology between the promoter sequences, whereas the CaMV and FMV promoters show about 47% homology. Similarly, by alignment of the region between the start of ORF1 to the end of ORF5, there is a 35% homology between CsVMV and CaMV as compared to a 56% homology between CaMV and FMV.

3. Protoplast Isolation, Transformation and Culture

Tobacco protoplasts were isolated from BY-2 (*Nicotiana tabacum* L, cv. Bright Yellow) cell suspension cultures and transfected with DNA essentially as described by Kikkawa et al, *J. Gen. Virol.,* 63:457-467, 1982.

Cassava protoplasts were prepared from *Manihot esculenta* L. cv TMS60444 embryogenic cell suspension cultures, Taylor et al, *Proceedings of the Second International Scientific Meeting of the Cassava Biotechnology Network—CBN II*, Bogor, Indonesia, pp 229-240, 1995. Fifty ml of a 10 day old culture (the medium was renewed every 2 days) was collected for protoplast isolation. Prior to enzymatic digestion, the cells were resuspended in 30 ml of medium containing 0.55 M mannitol, 3.2 g/l Schenk and Hilderbrandt salts (Sigma), 1× Murashige and Skoog vitamins (Sigma), 20 mM CaCl2, pH 5.8 [medium A]. The cells were allowed to settle and medium A was replaced by enzymatic solution consisting of medium A supplemented by 2% cellulase Onozuka RS and 0.1% Pectolyase Y 23. Digestion was performed in the dark for 3.5 h at 27° C. Cells were gently agitated during the first hour of treatment. The incubation mixture was filtered sequentially through sieves of 100 μm and 70 μm. Protoplasts were washed 3× by centrifugation at 100×g for 10 min in medium A. The number of protoplasts was estimated using an hemocytometer.

The purified protoplasts were resuspended to final density of $10^6$ cells m/l in electroporation buffer containing 5 mM Mes, 130 mM NaCl, 10 mM $CaCl_2$, 0.45 M mannitol, pH 5.8. Two hundred μl of electroporation buffer containing 30 μg of each plasmid prepared herein was added to 800 μl of protoplast suspension in a 0.4 cm path-length cuvette. DNA uptake was carried out using a Gene Pulser instrument (Biorad) delivering a 300 V pulse at a capacitance of 500 μF. After electroporation the protoplasts were incubated in ice for 30 min, after which they were resuspended at a density of $10^5$ cells/ml in culture medium A supplemented with 2% sucrose and $5\times10^{-5}$ M Pichloran. After 24 hours of incubation in the dark at 27° C., the protoplasts were collected by centrifugation (10 min at 100×g) and resuspended in GUS extraction buffer, Jefferson et al, *EMBO J,* 6:3901-3907, 1987, pH 7.7.

4. Plant Transformation with *Agrobacterium*

Gene constructs present in pBIN19 plasmids and prepared as described in the Examples were introduced into *Agrobacterium tumefaciens* strain LBA4404 by electroporation, Singh et al, *Focus,* 15:84-87, 1993. The modified *Agrobacterium* were used to infect *Nicotiana tabacum* cv *Xanthi* NN leaf discs, according to the procedure described by Horsch et al, *Plant Molecular Biology Manual*, pp. A5/1-A5/9. Kluwer academic publishers, Dordrecht, 1988. Regenerated kanamycin resistant plants were transferred to soil and grown in greenhouse. Seven independent transgenic lines containing the CVP1 construct and eight containing the CVP2 construct were produced. Greenhouse grown plants were allowed to self-fertilize and R1 seeds were collected. The R1 seeds were germinated on Murashige and Skoog (MS) medium, Murashige et al, *Physiol Plant,* 15:473-497, 1962, containing kanamycin and the seedlings were grown in greenhouse.

5. Plant Transformation Using Particle Bombardment

Leaves and stems were cut from cassava plantlets (cultivar Mcol 1505) grown in vitro on medium containing MS salts and vitamins, sucrose 20 g/l, CuSO4 2 μM, Phytagel 3 g/l, pH 5.7. The explants were sectioned and the tissue fragments were subsequently arranged in the center of 9 cm petri-dishes containing solidified culture medium. Micro-bombardment was performed with an helium-driven particle delivery system (PDS 1000/He-BioRad). Preparation of gold particles (average diameter 1.6 μm) and coating particles with DNA were carried out essentially as described by the instruction manual (BioRad). The target plates were placed in the gun chamber at the third level from the bottom while the assembly macrocarrier/stopping screen was placed at the fifth level. Each plate was shot twice at a pressure of 1100 PSI with approximately 1 g of plasmid DNA prepared as described in the Examples. After bombardment, sterile water was added to the plates to prevent desiccation of the material. Explants were incubated 2 days in the dark at 25° C. prior to histochemical GUS assays.

Seven transgenic rice lines (*Oryza sativa* L. Taipei 309) were obtained via particle bombardment as described by Li et al, *Plant Cell Reports,* 12:250-255, 1993, using pILTAB: CVP2 in association with pMON410 (Monsanto Co.); the latter carries the gene for resistance to hygromycin.

6. Luciferase and Glucuronidase Assays to Measure CsVMV Promoter Activity

Transfected protoplasts were lysed by vortexing for 2 min in GUS extraction buffer, pH 7.7. Extracts were clarified by centrifugation (5000×g, 5 min) at 4° C. in a microcentrifuge. The supernatant was recovered and used for MUG and LUC assays. GUS activity was determined using 4-methyl-umbelliferyl-β-D-glucuronide (MUG-Sigma) by the method of Jefferson et al, *EMBO J,* 6:3901-3907, 1987, and quantified for 50 μl of extract as pmol methylumbelliferone (MU) per hour. LUC activity was determined on 50 μl of the same protein extract with a luminometer (Monolight 2010) using a luciferase assay (Analytical Luminescence Laboratory, San Diego, Calif.). Cotransfection of cells with a uidA gene plus a luciferase plasmid allowed us to normalize variations of GUS activity between experiments, Leckie et al, *BioTechniques,* 17:54-57, 1994. The normalized GUS data were expressed as pmoles methylumbelliferone (MU) per hour per unit of light emitted.

Transgenic plant tissue were ground in GUS buffer, pH 8, and GUS activity was evaluated as described, Jefferson et al, *EMBO J,* 6:3901-3907, 1987. The enzyme activity (pmol/min) was refered to mg protein as determined by the dye-binding method of Bradford, M., *Anal. Biochem,* 72:248-254, 1976.

Histochemical analysis of GUS activity was performed essentially as described by Jefferson et al, *EMBO J,* 6:3901-3907, 1987. Small fragments of leaf and stem from primary transformants or R1 progeny were incubated at 37° C. for 4 to 8 hours in reaction buffer containing 1 mM 5-bromo-4-chloro-3-indolyl glucuronide (X-gluc), 100 mM sodium phosphate buffer, pH 7, 2 mM potassium ferrocyanide and potassium ferricyanide, and 0.1% Triton X-100. Roots and floral organs were incubated in the same medium lacking the cyanide salts and including 0.1 mercaptoethanol to reduce tissue browning. Hand-cut tissue sections were taken and cleared in 70% ethanol. Stained sections were visualized in a Zeiss microscope.

Figure 5:
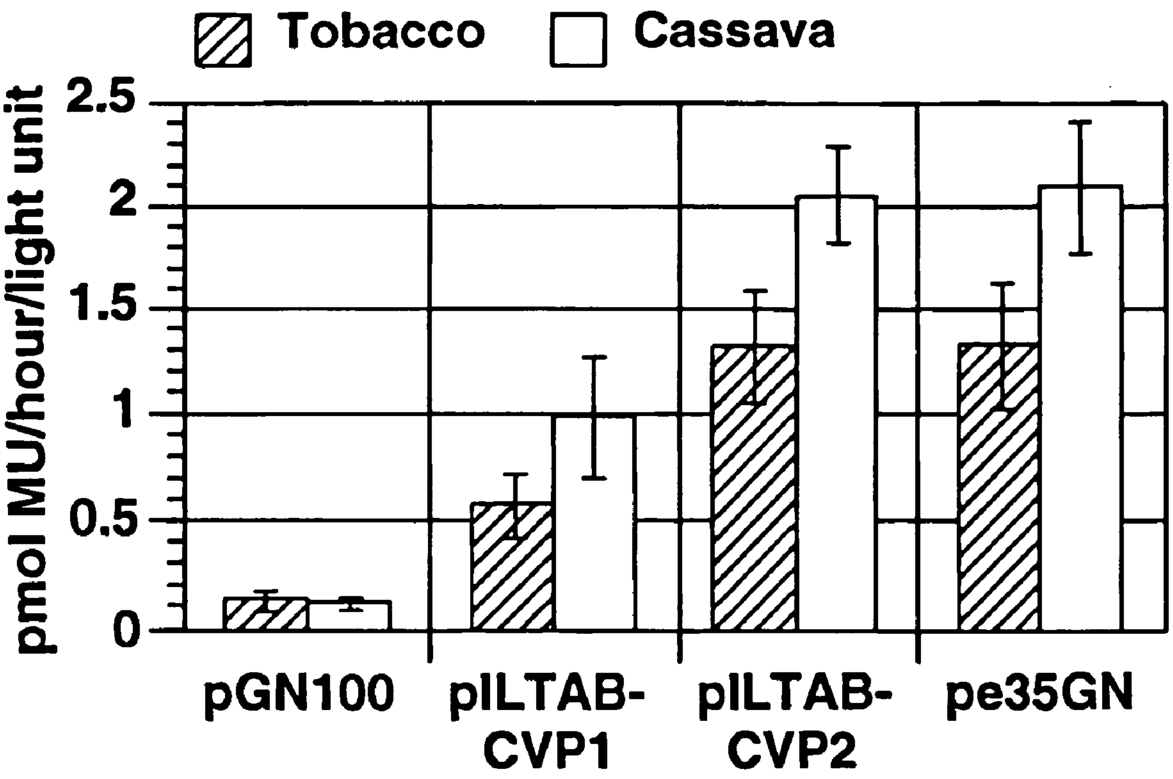
FIG. 5 illustrates expression of the CsVMV promoters in tobacco and cassava protoplasts as described in Example 7.a) Chimeric uidA gene constructs were co-introduced with a plasmid to express luciferase into protoplasts of cassava (stippled bars) and tobacco (crosshatched bars) via electroporation. Promoter activity is expressed as a ratio between GUS activity and LUC activity of the same protein extract. As a consequence, GUS activity is measured as pmol 4-methylumbelliferyl-β-D-glucuronide (MUG) per hour per unit of light emitted. Bars represent the average of four independent experiments +/− standard errors. Each experiment was carried out with a different protoplast preparation. pe35GN is a construct where the "enhanced" 35S promoter, Kay et al, *Science,* 236:1299-1302, 1987, controls the transcription of the uidA gene. pGN1OO is a control plasmid that contains a promoter-less uidA gene.

7. Expression of Exogenous Genes Using CsVMV Promoter a. Expression in Tobacco and Cassava Protoplasts Promoter fragments CVP1 and CVP2 were tested in transient assay experiments using tobacco and cassava protoplasts obtained from cell suspension cultures. In this experiment, we used the plasmids pILTAB:CVP1 and pILTAB: CVP2. The plasmid pe35GN, containing the uidA sequence under the control of the enhanced 35S promoter (e35S), Kay et al, *Science,* 236:1299-1302, 1987, served as a positive control. Each plasmid was cointroduced into protoplasts with a plasmid containing a luciferase gene under the control of the CaMV 35S promoter, Ow et al, *Science,* 234:856-859, 1986. The GUS/LUC ratio was determined after each transfection experiment. Four independent transfection experiments were carried out and gave similar results and are summarized in FIG. 5. In tobacco protoplasts the GUS/LUC ratio for the CVPL promoter was 0.58, or about 50% of the level of expression determined by the e35S promoter (1.32). However, when the CVP2 fragment was used, the ratio was 1.3, or two fold more active than CVP1. The difference between the two fragments indicates that CVP1 lacks one or more important element(s) for high level expression. CVP2 and e35S promoters yielded similar GUS activity indicating that the CsVMV promoter is a strong promoter in tobacco protoplasts. Similar studies in cassava protoplasts gave results comparable to those in tobacco showing that the CsVMV promoter is also very effective in these cells.

b. Expression in Tobacco and Rice Plants

Seven transformed tobacco lines containing CVP1 promoter-uidA gene fusion and eight containing CVP2 promoter were obtained as described herein. Presence of the full length gene cassette was confirmed by PCR analysis of primary transformants (plants regenerated from transgenic calli).

Figure 6A:
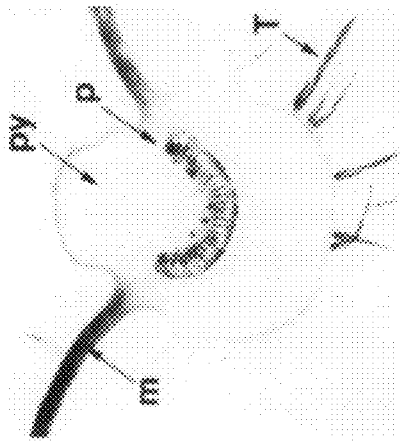
FIGS. 6A-6J illustrate histochemical localization of GUS expression in transgenic tobacco and rice plants containing a CsVMV promoter-uidA chimeric gene as described in Example 7 b). GUS activity is indicated in the transgenic tissues by a dark indigo dye precipitate after staining with X-Gluc. A: tobacco leaf section; B: detail of tobacco leaf section showing vascular tissues of the midrib (×10); C: transverse section through tobacco leaf lamina (×30); D: vascular tissues in tobacco stem cross-section (×30); E: tobacco roots (×10); F: transverse section through tobacco ovary (×10); G: rice leaf cross-section (×50); H: Cross-section of a rice leaf sheath (×50); I: rice flower split axially and subsequently stained for GUS activity (×10); J: GUS transient expression on cassava stem from in-vitro plantlet (×5). bs: bundle sheath; cy: chlorenchyma; ep: external phloem; ip: internal phloem; mx: metaxylem; p: phloem; ph: pith; pm: palisade mesophyll; pp: phloem parenchyma; py: parenchyma; rt: root tip; sc: sclerenchyma; sm: spongy mesophyll; x: xylem; xp: xylem parenchyma.
Figure 6B:
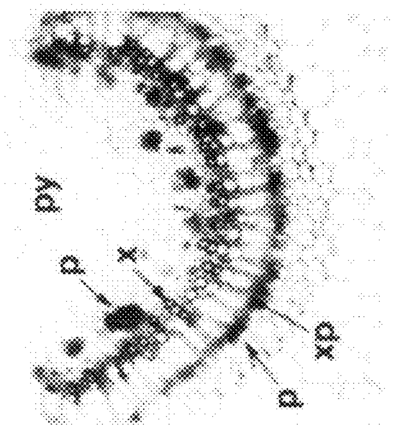
Figure 6C:
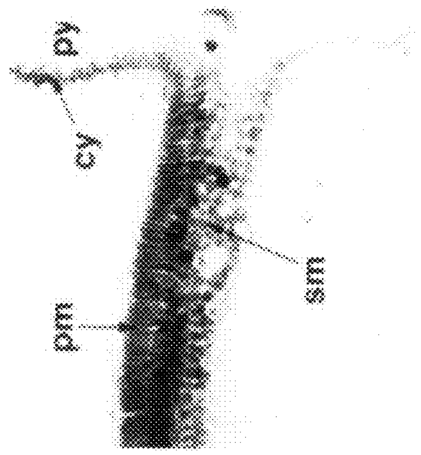
Figure 6D:
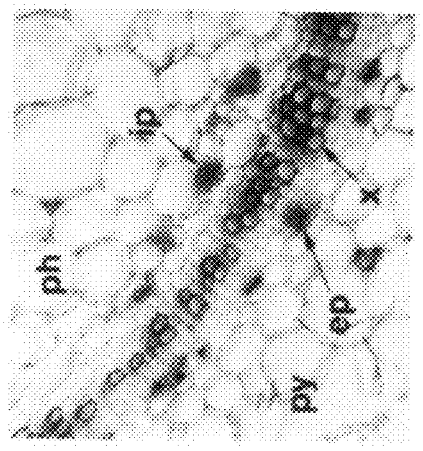
Figure 6E:
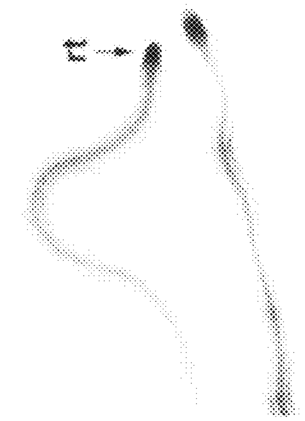
Figure 6F:
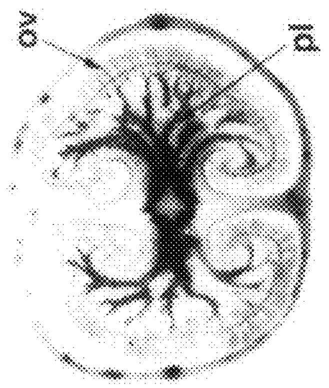

A detailed histochemical analysis of GUS accumulation was carried out using hand-cut fresh tissue sections of various organs from primary transformants and their R1 progeny. All transformed tobacco plants containing either the CVP1 or CVP2 fragment had essentially the same gene expression pattern while intensity of staining varied among transformants. In leaves, strong GUS activity was observed in phloem tissues in the midrib and in the lateral secondary veins (FIGS. 6A and 6B). Parenchyma cells adjacent to xylem elements also developed a blue staining pattern while the parenchyma cells of the midrib did not contain detectable GUS activity (FIGS. 6A and 6B) except for the chlorenchyma cells just below the epidermis (FIG. 6C). The cells of the palisade layer and the spongy mesophyll in the leaf lamina exhibited a very intense staining (FIGS. 6A and 6C), while in the epidermis, guard cells and trichomes, especially the glandular tip cell, developed an intense staining. Non-specialized epidermal cells accumulated little or no stain. Cross sections of stems showed strong staining of the phloem cells, including internal phloem bundles located in the central pith tissue and phloem cells located external to the xylem (FIG. 6D). Weaker expression was also visible in the xylem parenchyma cells. GUS staining was not detectable in pith cells or in cortical parenchyma cells of the stem (FIG. 6D). Root tissues incubated with X-Gluc revealed a blue stained vascular cylinder (FIG. 6E); cross-sections were not taken due to the fragile nature of the tissue. The root tips stained the most intensely of any region in the root (FIG. 6E). In the flowers, the basal part of the ovary exhibited an intense blue staining. The vascular elements of floral tissue displayed a strong staining in the stamen, the style and the placenta inside the ovary (FIG. 6F), as well as in the sepal and petals. Pollen grain exhibited also a blue color. R1 seedlings developed the same general pattern of staining as did the R0 parental transformant except that GUS activity in the mesophyl of cotyledons appear weaker than in mature leaves.

Figure 6G:
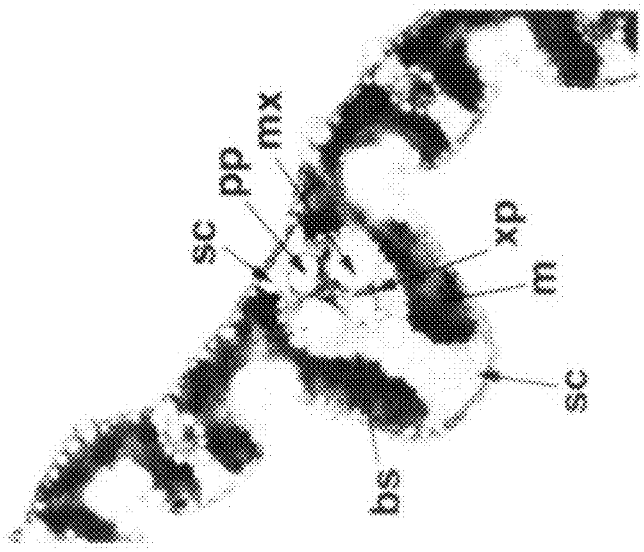
Figure 6H:
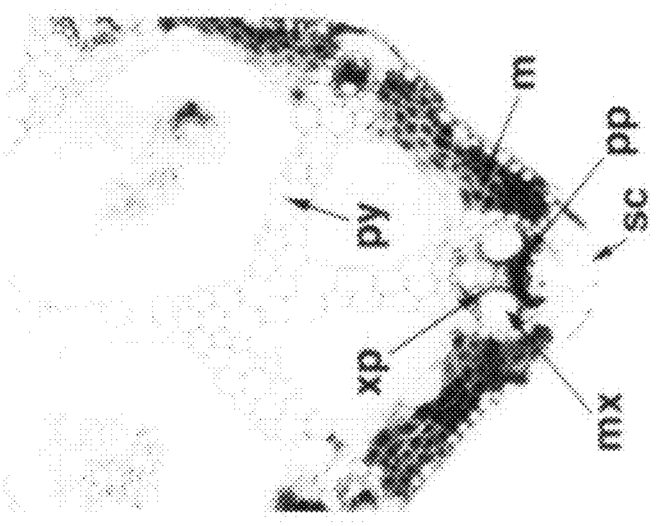
Figure 6I:
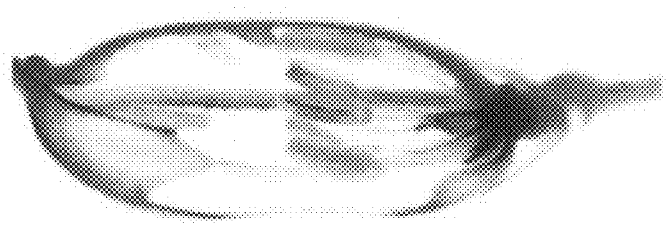

Histochemical analysis to detect GUS activity was performed in a similar manner on 7 independently transformed rice lines that harbor the CVP2:uidA gene. The general pattern of the CVP2 promoter-uidA gene was quite similar in rice and tobacco, despite the differences in anatomy of these plants. Transverse sections of leaves incubated with X-Gluc substrate resulted in strong staining in the vascular bundles and in the mesophyl cells (FIG. 6G). The small phloem parenchyma cells and the xylem parenchyma cells exhibited an intense staining while the metaxylem tracheary elements and the larger sieve elements appeared to be free of any blue precipitate. Bundle sheath cells, bulliform cells and sclerenchyma fibers also showed no staining. Guard cells and leaf hair cells were stained in the leaf epidermis. The pattern of GUS activity revealed in cross-sections of the leaf sheath tissue (FIG. 6H) was similar with that observed in leaves. As observed in tobacco plants, GUS activity was not detectable in parenchyma cells (FIG. 6H). Roots were stained only in the vascular cylinder and in the tip. Rice floral tissue had essentially the same pattern of GUS activity as the tobacco flowers (FIG. 6I).

Figure 7A:
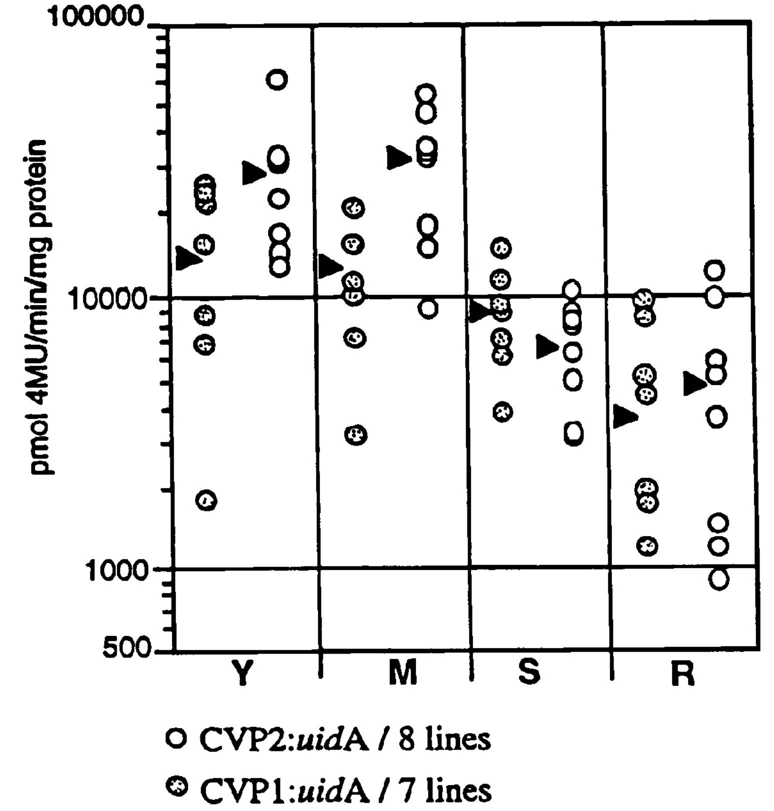
FIGS. 7A and 7B illustrate the quantitative distribution of GUS activity in different organ tissues among tobacco (A) and rice (B) transgenic plant lines expressed by the CsVMV/uidA chimeric gene as described in Example 7 b). Specific GUS activity is expressed as picomoles (pmol of 4-methyl umbelliferone (4MU) per milligram of protein per minute. Transgenic tobacco or rice lines containing either CVP1 (solid dots) or CVP2 (open dots) in a chimeric gene were assayed for GUS activity in young (Y) leaves 3 to 5 cm in length, mature (M) leaves 10 or more cm in length, stems (S), roots (R) and leaf sheath explants (ST). Samples for protein extraction were taken from mature (5-7 weeks old) R1 transgenic tobacco plants grown in a greenhouse. Rice plants used were R0 transformants (2 months old) grown in a greenhouse. Each dot represents a single independent transgenic line. The number of lines tested is indicated in the figure. Mean level of GUS activity in the different organs and for each construct is indicated by a solid arrow. The logarithmic scale was used to accommodate the large variation between lines.
Figure 7B:
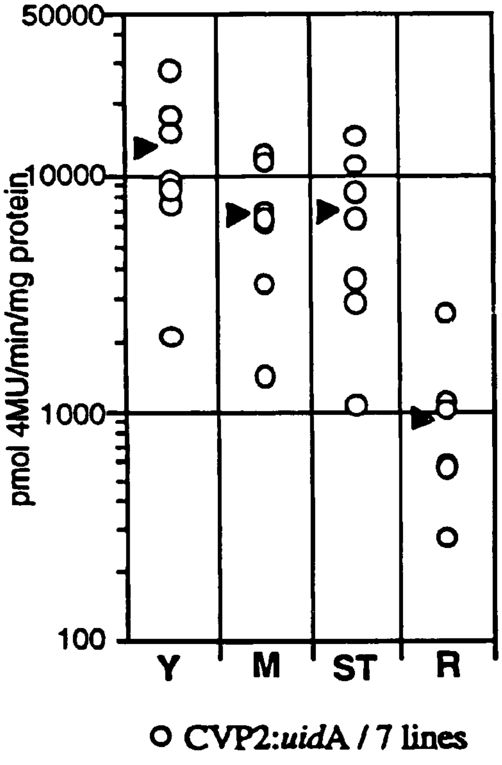

GUS activity in extracts prepared from different organs was determined quantitatively among tobacco and rice transformants prepared as described in the Examples and using the 4-Methylumbelliferyl-β-D-glucuronide (MUG) fluorescence assay, Jefferson et al, *EMBO J,* 6:3901-3907, 1987. The organs tested included young leaves, mature leaves, stem and root. The results of these assays are shown in FIG. 7 and confirm that the CsVMV promoter is active in all organs of both rice and tobacco. The CsVMV promoter is more active in leaves than in other organs while the lowest level of expression was in the roots. GUS activity in tobacco plants which harbor the CVP2 promoter does not appear significantly stronger than in plants containing CVP1 promoter. The two fold difference in promoter activity between CVP1 and CVP2 measured in protoplasts may not be detectable in transgenic plants due to variation of the transgene expression, relative variability of the MUG assay and great stability of GUS which lead to accumulation of protein in plants tissue.

c. Transient Expression in Cassava Plant Explants

Figure 6J:
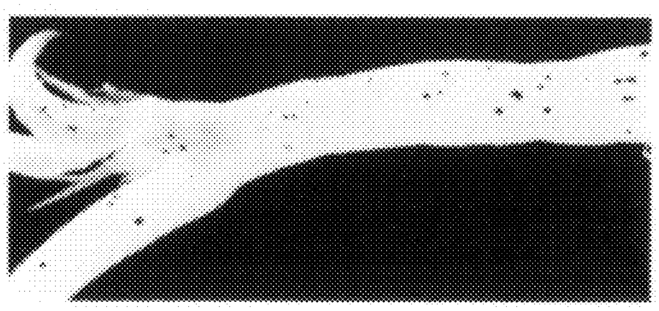

The promoter activity of the CVP2 fragment shown in FIG. 1 was tested in cassava plants by micro-particle bombardment on stem and leaf explants from material grown in vitro. The plasmid pILTAB:CVP2 and plasmid pe35GN (as positive control) were used in this study and transformation was conducted by bombardment as described in Example 5. Thereafter, the plantlets were analyzed for tissue expression by the histochemical method of Example 6. Approximately the same number of intensely blue-stained foci showing GUS expression (FIG. 6J) were found using plasmids containing either promoter. Blue-stained cells were found in epidermal cells, guard cells, mesophyl cells and along the veins of leaflets. These experiments provide evidence of promoter activity for CVP2 fragments in different cell types of cassava.

8. Discussion of Examples 1-7

The Examples describe isolation of a promoter from the viral genome of the newly characterized cassava vein mosaic virus, Calvert et al, *J Gen Virol,* 76:1271-1276, 1995. The transcription start site of the promoter was determined using RNA isolated from transgenic plants that contain the pCsVMV-uidA gene. The results here indicate that the CsVMV promoter is relatively strong in tobacco and cassava protoplasts and its activity is similar to that obtained with the e35S promoter. Of the two promoter fragments tested in protoplasts, the shorter fragment CVP1 is approximately two fold less active than the longer CVP2 fragment. However, both fragments result in the same pattern of expression in transgenic tobacco and rice plants. Differences in the level of expression observed in protoplasts could be due to a transcriptional enhancer in the 5' region of the larger fragment or to the larger untranslated leader sequence.

As a comparison, it is noted that the first 60 nucleotides of the CaMV leader (from +1 to the first ATG) stimulates expression of a downstream gene by about 2 fold (Dowson et al, *Plant Mol Biol,* 23:97-109, 1993; and Fÿtterer et al, *EMBO J,* 9:1697-1707, 1990). Similar effect has been reported for the untranslated leader of the rice tungro bacilliform virus (RTBV) promoter, Fÿtterer et al, *EMBO J,* 9:1697-1707, 1990. However there is limited sequence homology between the CsVMV leader and those of the CaMV or RTBV leaders. Analysis of transgenic plants indicate that the CsVMV promoter, as is the case with caulimovirus promoters, is active in all organs and in various cell types. The CsVMV promoter is strongly expressed in vascular tissues, in leaf mesophyll cells and in the root tips of rice and tobacco plants. However GUS activity was absent in non-chlorophyllous cells of tobacco pith and cortical parenchyma. This could indicate that the CsVMV promoter has two major domains of activity, i.e., the vascular elements and the green, chloroplast-containing cells. However we cannot exclude the possibility that these observations are due to the limitations of the staining assay. Large cells with little cytoplasm (such as parenchyma cells) may appear to contain little or no stain compared with smaller cells with dense cytoplasm. Likewise, cells with different metabolic activities may stain with different intensities.

The data herein shows that expression of the CsVMV promoter in protoplasts and transgenic plants is relatively similar to that of the 35S promoter. However the nucleotide sequence of the CsVMV promoter has limited homologies with caulimovirus promoters and may imply differences in the mechanisms of regulation of the promoter. Analysis of CsVMV promoter sequence shows the presence of several motifs that resemble previously identified cis-elements that are implicated in transcriptional regulation. The presence of such motifs in the CsVMV promoter could explain the pattern of expression in transgenic plants. A 16 bp motif with strong homology with the as1 element of the CaMV 35S promoter, Lam et al, *Proc Natl Acad of Sci USA,* 86:7890-7894, 1989, was identified in the CsVMV promoter at nt −203 to −219. The as1 element, characterized by TGACG direct repeats, binds to the AS1 nuclear factor, Fromm et al, *Plant Cell,* 1:977-984, 1989, as well as the cloned TGA1 transcription factor, Katagiri, et al, *Mol Cell. Biol,* 12:4809-4816, 1992, and directs root tissue specific gene expression, Benfey et al, *EMBO J,* 8:2195-2202, 1989. Expression of the CsVMV promoter in roots is similar to that induced by the CaMV 35S, Benfey et al, *EMBO J,* 8:2195-2202, 1989, and ComYMV promoters, Medberry et al, *Plant Cell,* 4:185-192, 1992, both of which contain the as1 element. In the CsVMV promoter, the as1 motif is located at position −203 to −219 while in the caulimovirus promoters, it is generally closer to the TATA box (n.t. −83 to −63 in the 35S CaMV promoter; −57 to −73 in the FMV promoter). However, in the ComYMV promoter, the as1 motif is located between nucleotide −205 and −227 and is not essential for root activity, Medberry et al, *Plant J,* 619-626, 1993: it is suggested that an additional element is involved in the regulation of the expression in roots of the ComYMV promoter. Additional studies are necessary to determine whether position of the as1 element relative to the TATA box sequence modulates its role in root gene expression.

At position −90 to −111, a 22 nucleotide sequence CTTATCACAAAGGAATCTTATC (SEQ ID NO 23) was identified that is present at the same relative position (n.t. −78 to n.t. −100) in the ComYMV promoter but not in other plant pararetrovirus promoters. This motif is located in the ComYMV promoter in a region required for expression in vascular tissues, Medberry et al, *Plant J,* 619-626, 1993. The CsVMV promoter also includes the motif AAGATAAGG (n.t. −186 to −194) which contains the boxI consensus GATAAG that is present in Rbcs gene promoters, Donald et al, *EMBO J,* 9:1717-1726, 1990. In addition, the sequence GTAGAAA, identified at position −257 −263, is identical to the binding site sequence for the MNF1 leaf-specific nuclear factor, found in the PEPc gene promoter as well as in the 35S promoter, Yanagisawa et al, *Plant Mol Biol,* 19:545-553, 1992. These motifs could be involved in the strong gene expression of the CsVMV promoters in mesophyl cells. Nucleotides −170 to −130 (FIG. 3) contain two motifs that are similar to the SV 40 enhancer core sequence GTGGAAAG, Ondek et al, *EMBO J,* 6:1017-1025, 1987.

9. Preparation of CsVMV Promoter Deletion Constructs

The CsVMV promoter was mutated by progressive 5' deletions and by internal deletions.

The starting plasmid for this study was pILTAB:CVP2 which contains a CsVMV promoter fragment extending from position +72 to −443, Verdaguer et al, *Plant Mol Biol,* 31:1129-39, 1996. Due to the absence of convenient restriction sites in the CsVMV promoter fragment, polymerase chain reaction (PCR) were used to generate a set of 5' terminal and internal deletions.

The 5' end deletions of the promoter were directly obtained by PCR amplification. We used a common reverse primer P1' (Table 1) which hybridizes at the 3' end of the promoter paired with CsVMV specific primers P2, P3, P4, P5 and P6 (Table 1) to generate five promoter fragments designated B, C, D, E and F having various deletions of the wild-type CsVMV promoter sequence.

TABLE 1

| Name | Sequence (5' to 3') | Position | Sense | SID |
|---|---|---|---|---|
| P1 | GC**TCTAGA**CCAGAAGGTAATTATCCAG | −443/−423 | + | 24 |
| P2 | TAT**GGATCC**TATGTTCAAAAATGAAG | −330/−312 | + | 25 |
| P3 | AAA**GGATCC**TGAAGACGTAAGCACTG | −222/−206 | + | 26 |
| P4 | AGA**GGATCC**GGTCGGTGATTGTGAA | −178/−163 | + | 27 |
| P5 | AAA**GGATCC**TTATCACAAAGGAATC | −112/−95 | + | 28 |
| P6 | TAT**GGATCC**GTGTCATTTTTGCCCTTG | −63/−43 | + | 29 |
| P1' | CG**GAATTC**AAACTTACAAATTTCTCTAAG | +72/+50 | − | 30 |
| P2' | TAA**GGATCC**TTTCCGCCCTTACATT | −116/−132 | − | 31 |
| P3' | CAT**GGATCC**TCTATGTCTCTTTCAC | −149/−168 | − | 32 |
| P4' | ACA**GGATCC**GACCTTATCTTCT | −173/−187 | − | 33 |
| P5' | ACC**GGATCC**TCTTCTTTTCATTGTTC | −182/−199 | − | 34 |
| P6' | TCA**GGATCC**TTTTCTTCGCCTGGT | −228/−243 | − | 35 |
| P7' | ATA**GGATCC**ATATGTGCCGCATA | −334/−348 | − | 36 |

Table 1 illustrated oligonucleotide primers used to generate CsVMV promoter fragments by PCR amplification. "SID" indicates SEQUENCE ID NO. Primers contain CsVMV promoter sequences in sense (+) or reverse orientation (−). Coordinates of the primers relative to the transcription start site shown in FIG. 3 are noted. The primers P1' in association with P2 to P6 were used to create 5' terminal deletions of the CsVMV promoter. Similarly, P1 in association with P2' to P7' were used for 3' end deletions. P1 and P1' contain respectively a XbaI and a EcoRI site at their 5' ends while other primers have a BamHI site. Restriction sites are indicated by bold letters.

The oligonucleotide primers in Table 1 were prepared by phosphoramidite chemical synthesis on an automated synthesizer by a commercial vendor (GIBCO BRL LIFE TECHNOLOGY, INC.).

Figure 8:
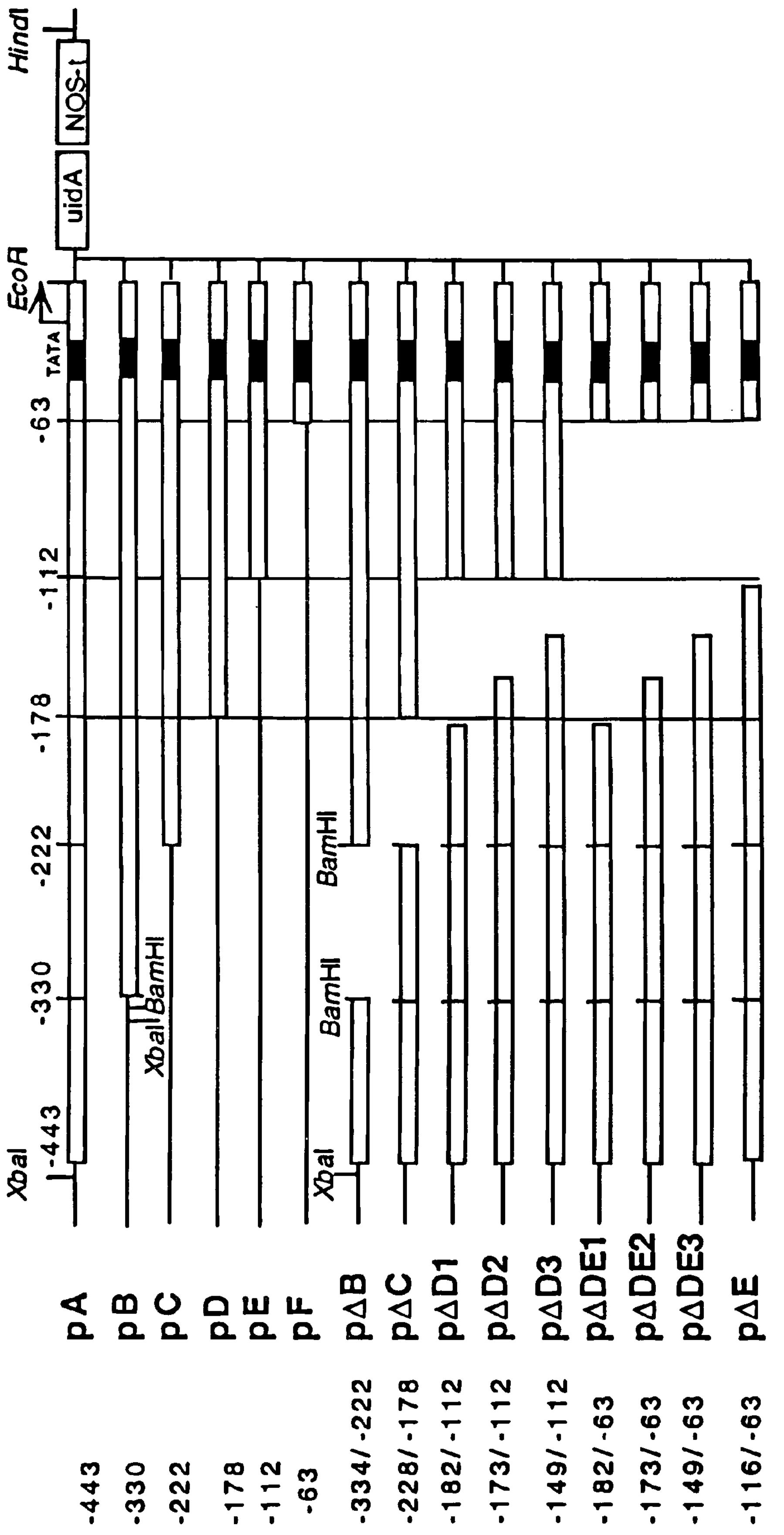
FIG. 8 illustrates a schematic representation of the various chimeric CsVMV promoter/uidA gene fusion expression constructs prepared as described in Example 9. The names of the different plasmids containing the constructs and the end points of the 5' and internal deletions in the constructs are indicated on the left side of the figure. Internal deletions are indicated by the symbol "Δ". pA contains the full length CsVMV promoter illustrated in FIG. 3. All 5' end deleted promoters have a BamHI site at their 5' ends. Internal deletions were created by BamHI ligation of the 5' end truncated promoters with 3' end deleted promoter fragments.

The resulting PCR-amplified fragments have a common 3' end at position +72 and their 5' end points at positions −330, −222, −178, −112, −63 respectively (FIG. 8). A full-length promoter fragment (A fragment) was also re-synthesized using the primer P1 and P1' (Table 1). PCR reactions were carried out with 100 ng of pILTAB:CVP2, 2.5 U of Taq DNA polymerase (GIBCO BRL) and standard concentrations of primers, MgCl2 and dNTPs. Twenty cycles (94° C., 30 s; 56° C., 30 s, 72° C., 30 s) of amplification were performed and were followed by 5 min of final elongation at 72° C. Each of the five amplified DNA fragments was digested by BamH1 and EcoRI and ligated into the same sites of a plasmid containing the coding sequence of the uidA gene (coding for the β-glucuronidase-GUS) linked to the 3' polyadenylation signal of the nopaline synthase gene (FIG. 8). The resulting plasmids were named pA, pB, pC, pD, pE, pF according to the promoter deletion they carry (FIG. 8).

The internal promoter deletions were constructed in two steps. First, PCR condition were performed as described above to generate a set of 3' deletions of the CsVMV promoter. A sense primer (P1, Table 1) which hybridizes at the 5' end of the promoter was paired with each of 6 specific CsVMV reverse primers (P2' to P7', Table 1) to generate six truncated promoters with a common 5' end at position −443 and 3' end points spanning from position −116 to −334. Then, internal deletions were engineered by cloning the different 3' end truncated promoter fragments upstream of the 5' end deleted promoters into the plasmids previously obtained (pB to pF). Accordingly, a 3' deleted promoter fragment encompassing nucleotides −443 to −334 was digested by BamH1 and XbaI and ligated to the same sites in the pC plasmid. The resulting plasmid named pΔB contains an internal deletion from nucleotides −334 to −222 (FIG. 8). Similarly, a fragment spanning nucleotides −443 to −228 was fused to the D promoter fragment to create the plasmid pΔC (FIG. 8). Three fragments with a common 5' end at −443 and 3' ends located at position −182, −173, and −149 were cloned individually into the plasmid pE to create the plasmid pΔD1 and pΔD2 and pΔD3, respectively (FIG. 8). The same three fragments were cloned into pF to create the plasmid pΔDE1 and pΔDE2 and pADE3 (FIG. 8). A fragment containing nucleotides −443 to −116 was cloned with the same method in the plasmid pF to generate the plasmid pΔE (FIG. 8). All promoter sequences were verified by di-deoxynucleotide sequencing. The different CsVMV promoter-uidA fusion genes were excised by XbaI and HindIII and ligated to same sites of pBin 19 binary vector used for *Agrobacterium*-mediated plant transformation.

10. Expression Analysis of CsVMV Promoter Deletion Constructs a. Transformation of Plants With *Agrobacterium*

The pBin 19 derived plasmids carrying the deleted promoter constructs were transferred by electroporation into *Agrobacterium tumefaciens* strain LBA4404. *Agrobacterium*-mediated transformations of *Nicotiana tabacum* cv *Xanthi* NN were performed as previously described, Horsch et al, *Plant molecular biology manual*, pp. A5/1-A5/9. Kluwer academic publishers, 1988. Regenerated kanamycin resistant plants were grown to maturity in a green-house and allowed to self-fertilize. R1 seeds were germinated on Murashige and Skoog (MS) culture medium, Murashige & Skoog, *Physiol Plant,* 15:473-497, 1962, with 100 mg/l kanamycin and transferred to soil in a green house. Between 10 and 20 independent transgenic lines were produced for each construct. Ten independent R1 lines for each promoter construct were analyzed.

b. Histochemical Analysis of CsVMV Expression in Young Seedlings

A histochemical GUS analysis on plasmid-transformed 10 days old seedlings was carried out in order to analyze the expression pattern of the deleted promoter at earlier stages of development.

The young expanded leaves at the top of the plants were collected for GUS analysis. Fresh tissue sections were taken and incubated for 6 to 12 hrs at 37° C. in reaction buffer containing 1 mM 5-bromo-4-chloro-3-indolyl glucuronide (X-gluc), 100 mM sodium phosphate buffer pH 7.2 mM potassium ferrocyanide and potassium ferricyanide, and 0.1% Triton X-100. For the GUS histochemical analysis of young R1 seedlings, the whole plantlets were collected around one week after germination and immersed in GUS buffer, Jefferson et al, *Embo J,* 6:3901-7, 1987. After few minutes of vacuum infiltration incubation was carried out overnight at 37° C. Samples were cleared by several washes in ethanol 70%. Quantitative GUS analysis using the substrate 4 methylumbelliferone-β-D glucuronide (MUG) were performed as described by Jefferson et al, *Embo J,* 6:3901-7, 1987.

Expression patterns of the different promoter constructs were analyzed in transformed transgenic tobacco plants using histochemical staining of GUS activity. The presence of an intact promoter:uidA gene cassette was confirmed by PCR and/or Southern analysis. The GUS expression pattern observed between plants containing the same promoter construct was similar, with the few exceptions reported below. Significant and reproducible differences in the staining intensities between some promoter constructs could be clearly visualized. The plants tested in this study contained between 1 to 5 copies of the uidA fusion gene. The copy number did not affect the characteristic pattern of expression observed with each construct. Moreover no clear correlation was noticed between the copy number and the apparent intensity of the staining. Different staining patterns, between promoter constructs indicated an effect of the deletion on the promoter regulation. The CsVMV promoter is expressed in all organs of a transgenic plants. Regions of highest promoter expression were located in the vascular elements, the mesophyll cells of the leaves and the root tips. Accordingly, GUS activity was analyzed in these three different tissues and the results are summarized in Table 2.

TABLE 2

| Promoter | | Mesophylls | Phloem | Root tips |
|---|---|---|---|---|
| −443 | pA | + | + | + |
| −330 | pB | + | + | + |
| −222 | PC | + | + | + |
| −178 | pD | (+) | + | − |
| −112 | pE | + | (+/−) | − |
| −63 | pF | + | − | − |
| −334/−222 | pΔB | + | + | + |
| −228/−178 | pΔC | + | + | + |
| −182/−112 | pΔD1 | + | + | + |
| −173/−112 | pΔD2 | + | + | + |
| −149/−112 | pΔD3 | + | + | + |
| −182/−63 | pΔDE1 | − | (−) | + |
| −173/−63 | pΔDE2 | − | (+/−) | + |
| −149/−63 | pΔDE3 | − | (+/−) | + |
| −116/−63 | pΔE | + | + | + |

Figure 9A:
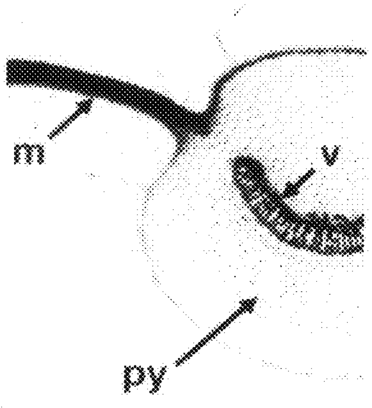
FIGS. 9A-9I illustrate the histochemical localization of GUS expression in transgenic tobacco plants containing CsVMV promoter/uidA chimeric gene deletion constructs as described in Example 10 b). All pictures are cross-sections of young expanded leaves from 5 week old transgenic tobacco plants, except for pictures h and I. a) pB; b) pD; c) pE; d) pΔC; e) pΔD1; f) pΔDE1; g) pΔDE2; h) leaves from 10 day old transgenic seedlings carrying the pB construct (right) or pD construct (left); I) roots from transgenic tobacco plants containing the pC construct (top) or pD construct (bottom). m: mesophyll; v: vein; py: parenchyma; RT: root tip.
Figure 9B:
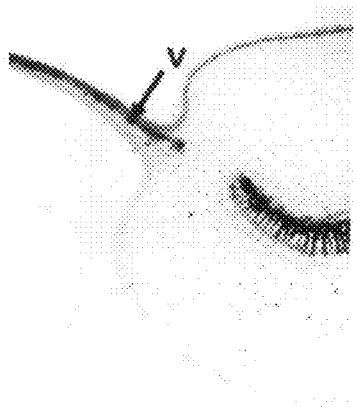
Figure 9C:
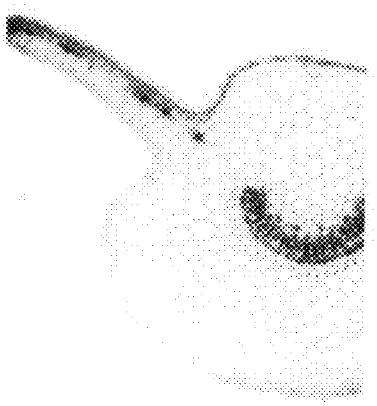

The promoter construct names and end-points of the deletions are indicated for each construct shown in Table 2. GUS activity expression levels detected are scaled and reported in Table 2 in four levels: "+": no visible difference with the full length promoter (i.e., pA); "(+/−)": lower staining than with the full length promoter; "(−)": very little expression; "−": no detectable staining.

a) 5' End Deletions:

GUS staining in transgenic plants carrying the promoter construct deleted to the position −222 (constructs pC) occurred in the same pattern (Table 2) and was in the same range of intensity as what was observed with the full length promoter (construct pA, FIG. 9A). Further deletion of the promoter to the position −178 (construct pD) caused an important change in the GUS expression pattern (Table 2). In leaf cross-sections of most of the plants carrying the pD construct, a strong staining restricted to the vascular elements was observed (FIG. 9B). No detectable GUS activity was detected in the palisade and spongy mesophyll cells. Three plants lines out of ten however, presented a low staining in the mesophyll cells. In all plants transformed with the pD construct, the root tips did not exhibit GUS staining (FIG. 9I0), while this tissue is intensely stained with the full-length promoter. GUS expression from the promoter construct pE, deleted to position −112, was restricted to the vascular elements (Table 2, FIG. 9C). The intensity of the expression was very low and long incubation time was required to detect a blue precipitate. The construct pF (SEQ ID NO 8) did not display any detectable expression. This study showed that organ specific functions can be attributed to distinct promoter regions. While the region spanning nucleotides −443 to −222 appeared to be non-essential for promoter activity, the region from −222 to −178 is apparently responsible for promoter expression in mesophyll cells as well as in the root tip. Consequently a promoter deleted to the position −178 is nearly inactive in green tissue although it contains all the elements necessary for vascular expression. The pE construct was shown to display a very weak vascular expression. The strong vascular expression visualized with the pD construct could be either due to a strong vascular element in the (−178/−112) region or to a non-specific activator present in this region which influences the vascular element present in the pE promoter.

b) Internal Deletions

Figure 9D:
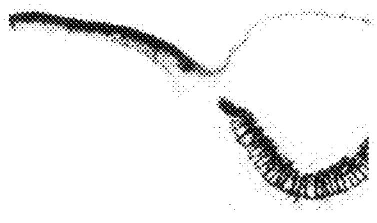
Figure 9E:
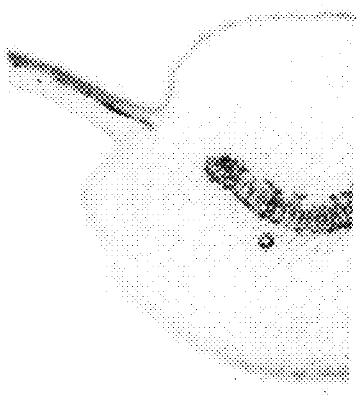
Figure 9F:
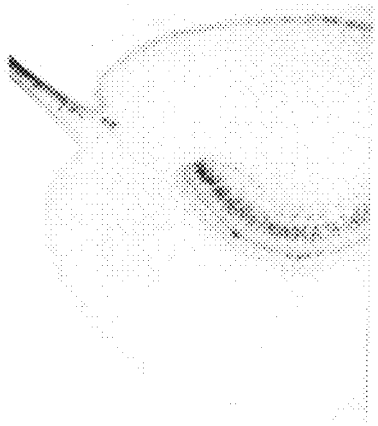

Internal deletion of the region from nucleotide −334 to −222 (promoter ΔB) did not affect the general expression pattern of the CsVMV promoter (Table 2). A significant decreased in GUS expression was visualized in the mesophyll tissue of the plants transformed with pΔC (Table 2, FIG. 9D). In agreement with the data obtained from 5' end deletion, this result showed that the −222 to −178 region contains important elements that control promoter expression in green tissues. However, a low staining in mesophyll cell is observed in all lines tested suggesting that an additional element of lower importance, presumably located in the region encompassing nucleotide −443 to −222, is also involved in promoter expression in this cell type. Additionally, the vascular elements showed a strong staining suggesting that the promoter activity in this tissue was not affected by this deletion (FIG. 9D). The pΔC construct did not suppress expression in the root tip. This suggested that in addition to the (−222/−178) region, another element located in the (−443/−222) region is probably involved in promoter expression in this tissue. Deletion of the region from −182 to −112 (construct pΔD1) had a dramatic effect on promoter expression (Table 2). Indeed, the construct pΔD1 displayed a vascular specific profile of expression with only weak staining in vascular elements (FIG. 9E). Additionally, GUS expression was also observed in the root tip. This promoter construct contain most of the domain implicated in mesophyll tissue expression as defined earlier. This mesophyll domain, in the context of the ΔD1 deletion failed to activate the promoter in the green tissue. This result could be due to the deletion of one or more cis-elements located between the nucleotide-182 and −112 and needed for promoter activation of the mesophyll domain. The construct pΔE displayed a constitutive pattern of expression similar to the non deleted promoter (Table 2, FIG. 9G). The strong vascular expression observed with this construct suggested that the vascular element mentioned earlier which is present in the (−112/−63) region is not required for strong promoter expression in vascular tissue. Therefore, an important vascular function can be attributed to the region (−178/−112). The internal deletion encompassing nucleotides −182 to −63 (pΔDE1) had a profound effect on promoter activity (Table 2). Of the 10 independent transgenic plant tested, 8 did not have any detectable GUS activity in the leaves and in stems. Very pale blue punctuation localized in the phloem elements were visualized in two plants after prolonged incubation (FIG. 9F). In contrast, a strong staining was revealed in the root tip as well as weaker staining in the vascular elements of the root. These results are somewhat in agreement with the data mentioned above. Indeed, the ΔDE1 promoter does not contain the region for vascular expression (−178 to −63) as well as a region which is required for expression in the mesophyll tissue (−182 to −112). The GUS activity detected in root tissue is presumably due to the presence of the (−443/−182) region which was shown to be involved in the root tip expression.

c) The (−178 −112) Promoter Domain.

Figure 9G:
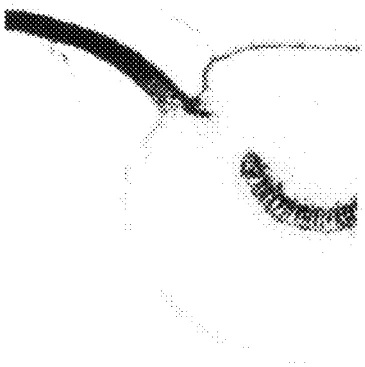

The results of the 5' end deletions emphasized the importance of the (−182/−112) region for the constitutive expression of the CsVMV promoter; The deletion pΔD1 indeed suppressed promoter activity in the mesophyll tissue and also diminished the vascular expression (FIG. 9E). Consequently, we made the construct pΔD2 and pΔD3 to investigate this region in greater details (Table). The construct ΔD2, deleted from nucleotides −173 to −112, displayed a profile of expression similar to the full length CsVMV promoter (FIG. 9G). This result suggested that the addition of 9 nucleotides at the 5' end point of the (−182/−112) deletion could restore the full expression pattern altered with the construct ΔD1. Interestingly theses 9 nucleotides contain a GATA motif. The most dramatic difference was observed in mesophyll cells, which did exhibited any blue color when transformed with the ΔD1 construct. The region from −182 to −173 is thus necessary for mesophyll expression. No significant difference could be detected between the construct pΔD2 and pΔD3.

In contrast, addition of the sequences −182/−173 and −182/−149 to pΔDE1 to make pΔDE2 and pΔDE3 respectively, did not lead to a restoration of promoter activity (Table 2) except in root tips. In plants transformed with pΔDE2 and pΔDE3, GUS staining was not observed in mesophyll cells while expression in vascular elements was very low (FIG. 9E). The comparison of the constructs pΔD2 and pΔD3 with the constructs pADE2 and pΔDE3 implied an important role of the (−112/−63) region for the general promoter activity. However, the dramatic effect of the deletion of this region could be suppressed by the addition of the (−149/−116) region as suggested when comparing pΔDE3 with pΔE (Table 2, FIGS. 9E and 9G). These results indicated that the upstream region from −222 to −173 could not alone achieve a full constitutive pattern of expression. The presence of either the (−149 to −116) region (shown by pΔE) or the region from −112 to −63 (shown by pΔD2 and pΔD3) which could be functionally redundant, in association with the upstream region (−222 to −173) are necessary for optimal activity of the CsVMV promoter in all tissues.

Our results indicate (as shown comparing pΔE and pΔDE3) that the (−149/−116) region is probably responsible for the strong vascular expression observed with the truncated promoter D.

Figure 9H:
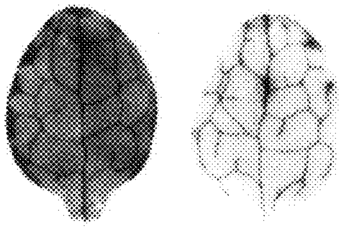
Figure 9I:

The deleted promoter constructs directed specific expression patterns which were similar to those observed in adult plants. In cotyledonary leaves, the constructs pD, pE, pAD1, which conferred a vascular specific expression pattern in expanded leaves of adult plants exhibited a GUS staining profile only in the vascular elements (FIG. 9H). Similarly, the pB and pC constructs which were active in both mesophyll and vascular tissues in tobacco plants had the same constitutive expression pattern in seedlings (FIG. 9H). These results suggested that specific expression patterns observed with the different deletions in transgenic plants are not influenced by the developmental stage of the plant.

c. Expression in Transgenic Seedling Plants

Figure 10:
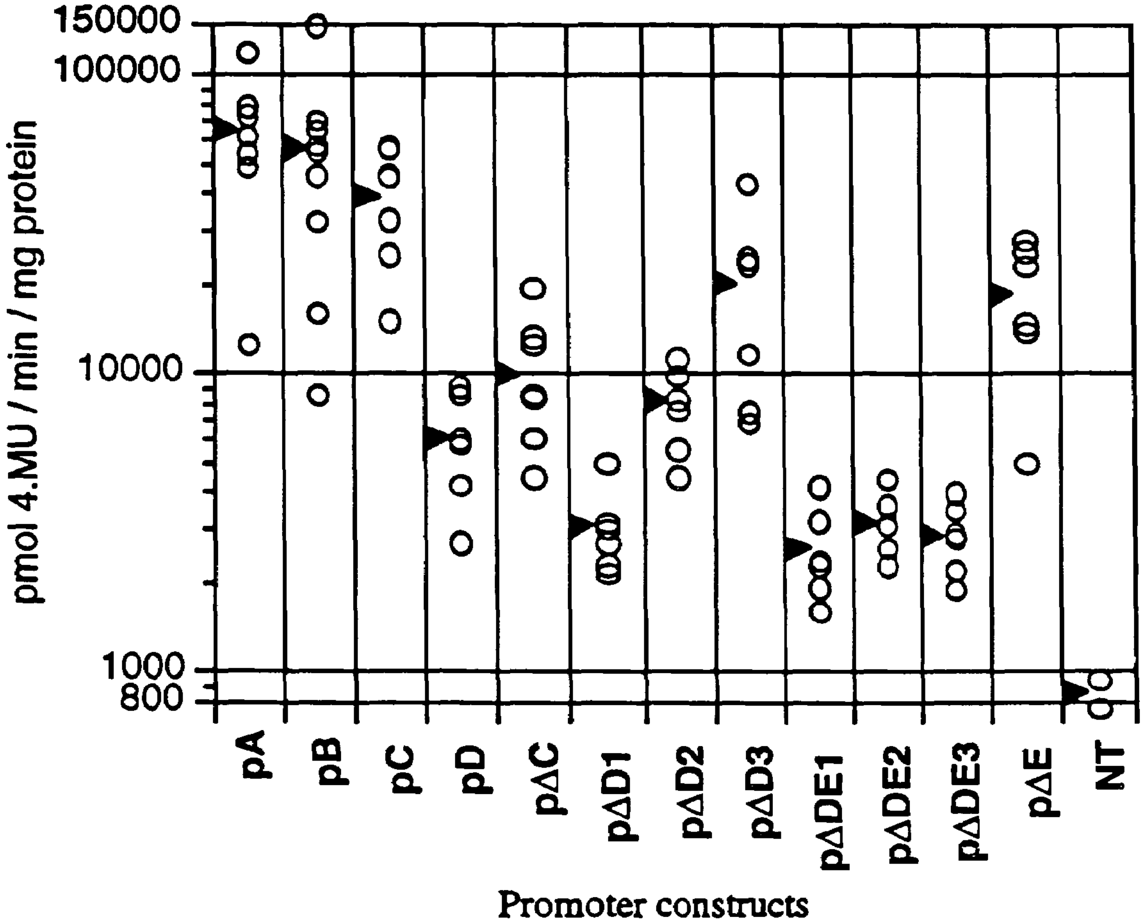
FIG. 10 illustrates GUS enzyme activity in transgenic tobacco leaves expressed by CsVMV promotor/uidA chimeric gene deletion constructs as described in Example 10 c). Proteins were extracted from leaf discs collected from young explanted leaves of 5 weeks old transgenic plants. For each construct, 6-10 independent transgenic lines were assayed for GUS activity. The data are expressed as described in FIG. 7. Results from each plant is shown as an open dot. Each different promoter construct is indicated separately. The average GUS level in indicated by a vertical arrow. A logarithmic scale was used to accommodate the large variation between transgenic lines.

GUS activities in protein extracts prepared from leaf tissues were quantitatively measured using a fluorometric assay, Jefferson et al, *Embo J,* 6:3901-7, 1987. The samples were collected from interveinal tissue of young expanded leaves from 5 week old transgenic tobacco plants prepared as described in Example 10.a). Consequently, the enzyme activity levels detected reflected mainly the promoter expression in mesophyll tissue. As it is shown in FIG. 10, the values of GUS activities of different transgenic lines carrying the same promoter construct varied by a maximal factor of 17. The variation in transgene expression can be attributed to a combination of factors including a putative position effect reflecting the influence of the surrounding chromatin on gene expression, differences in copy number or gene silencing. These data confirm the histochemical localization data for GUS expression in transgenic plants. The lowest GUS activity levels were detected in extracts from plants carrying the promoter constructs pΔD1, pΔDE1, pΔDE2 and pΔDE3. This result was consistent with the histochemical analysis since these deletion constructs did not express the reporter gene in mesophyll cells of transgenic plants but displayed a weak GUS staining in vascular elements. Accordingly the GUS activity levels of these deletions were about 20 fold lower than the levels detected with the constructs pB and pC which exhibited strong constitutive expression patterns in transgenic plants. A significant drop in the level of activity was found if the sequence from −222 to −178 was deleted as shown by the construct pD. Similarly, the internal deletion of the sequence from −228 to −178 reduced by a factor five the level of GUS activity measured with the high expressing constructs pB or pC. These results emphasized the role of the region from nucleotides −228 to −178 for promoter expression in green tissues.

The average level of activity measured with the construct pΔD2 and pΔD3 was higher than with the pΔD1 construct. However the pΔD3 activity levels were in the higher range while the construct pΔD2 gave moderate levels of expression. This difference was not detected using the histochemical assay. The construct pΔD2 was expressed in mesophyll cells of transgenic plants but based on the fluorometric assay it is possible that the GUS staining observation overestimated the level of activity of this promoter construct. Consequently the fluorometric GUS measurements suggested that the region encompassing nucleotides −173 to −149 is important for the level of expression in green tissues. As observed with the histochemical assay, the high expression level measured with the construct pΔD3 was abolished by deletion of the region spanning nucleotides −112 to −63 (construct pΔDE3). However, high levels of GUS activity were measured despite a deletion of the region containing nucleotides −116 to −63 (construct pΔE) indicating that the region from −149 to −116 is useful for high levels of promoter activity (as shown when comparing pΔDE3 and pΔE).

d. Protoplast Isolation, Transformation, and Culture

Protoplasts from BY-2 tobacco suspension cells were prepared and transfected with DNA essentially as described by Watanabe et al, *FEBS Letters,* 219:65-69, 1987. Tobacco mesophyll protoplast were isolated from fully expanded leaves of 5 weeks old plants grown in a growth chamber. The leaves were surface sterilized by immersion in a 5% chlorox solution during 5 min followed by 3 washes with sterile water. The leaves were dried in a laminar hood and the lower epidermis was removed by peeling. The peeled leaf pieces were washed in 0.6 M mannitol and transferred to an enzymatic solution containing 1.5% cellulase R10, 0.3% macerozyme R10, and 0.6 M mannitol pH 5.8. Digestion was carried out at 28° C. for 12 to 16 hrs. The digestion mixture was filtered through one layer of Miracloth and subsequently centrifuged for 10 min at 300 rpm in a clinical centrifuge. The supernatant was collected and centrifuged a second time with the same settings. Protoplast pellets were resuspended in 20% sucrose solution and transferred to 50 ml volumetric flasks. The flasks were centrifuged in a J6B Beckman rotor at 100 g for 7 min. Intact round shaped protoplasts floating at the surface of the sucrose solution were collected with a Pasteur pipette and counted using an haemocytometer. About 1 million protoplasts were used for each electroporation.

Mesophyll protoplasts were resuspended in 600 μl of electroporation buffer containing 0.55 M mannitol, 5 mM MES, 70 mM KCl, pH 5.8. Thirty μg of plasmid DNA with 30 μg of 35S-luciferase construct, Ow et al, *Science,* 234:856-859, 1986, used as an internal standard were added to the protoplast solution and the DNA transfer was carried out at 200 volts and 250 μF using a BioRad gene pulser apparatus. After the pulse, the protoplasts were allowed to settle for 1 hr on ice. Protoplasts were cultivated at a density of $10^5$ cells/ml in a culture medium containing 0.4 M mannitol, 30% sucrose, 4.3 g/l MS salts, 10 mg/l thiamine HCl, 5 mg/l nicotinic acid, 10 mg/l pyridoxine HCl, 100 mg/l myoinositol, 2 mg/l glycine, 2 mg/l NAA, 0.5 mg/l BAP, pH 5.8. Protoplasts were collected for protein extraction after 24 hrs of culture at 25° C.

MUG and LUC assays were performed on the protoplast protein extracts as described above. Results were expressed as a ratio between the GUS activity of the CsVMV promoter construct and the LUC activity of the internal control.

e. Expression of the CsVMV Promoter Constructs in Protoplasts

Figure 11:
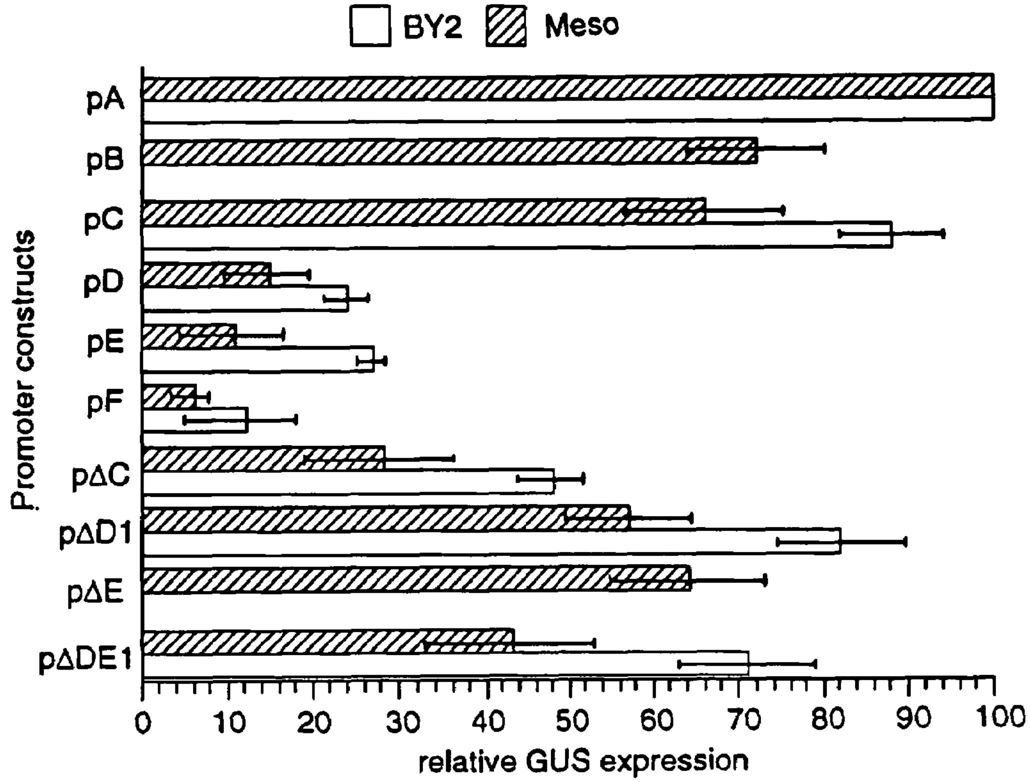
FIG. 11 illustrates transient GUS expression by CsVMV promoter/uidA chimeric gene constructs in BY-2 (cross-hatched bars) and leaf mesophyll (diagonal striped bars) protoplasts as described in Example 10 e). Electroporated protoplasts prepared from BY-2 cell suspension or from tobacco leaves were analyzed for GUS activity after 24 hours of culture. The various indicated promoter constructs were cotransfected with a luciferase plasmid as an internal standard. GUS expression levels were normalized in relation to the luciferase expression and expressed as a percentage relative to GUS expression using full-length promoter activity in which a 100% value was assigned to the construct pA. Each bar each represents the average of four independent experiments, with +/− standard errors also shown.

Protoplasts prepared from BY-2 suspension cells as well as mesophyll cells from tobacco leaves were transfected with the CsVMV promoter constructs as described in Example 10. Transient expression of GUS was measured as described in Example 6 at 24 h after electroporation in relation to an internal standard expressed from a cotransfected luciferase plasmid. Four independent transfection experiments for each protoplast system were carried out. The results obtained are summarized in the FIG. 11.

In BY-2 protoplasts, the construct pC which contains a CsVMV promoter deleted to position −222 retained 88% of the activity of the full length promoter fragment. The promoter activity dropped sharply to only 24% of full activity with a further deletion to position −178. Constructs pD and pE had almost the same expression level while a second drop of activity was observed with a deletion extending to position −63. The construct pF with 12% of the full promoter activity was just above the background level. An internal deletion from nucleotide −228 to −178 (construct pΔC) decreased the total expression by more than 50%. Surprisingly the constructs pΔD1 and pΔDE1 which gave very low expression in transgenic plant allowed high levels of expression. This results contrasted sharply with what we observed in plants and could possibly reflect differences in cell type used in the two systems, i.e. differentiated cells from intact plants versus undifferentiated cells from cell culture. To address this question we undertook transfection experiments using leaf mesophyll protoplasts. The 5' deletions from −443 to −222 (construct pC) lead to a 35% decreased in promoter expression. The GUS activity from the construct pD was only 15% of that from the full length promoter, while level of activity from the construct pF was not above background. As for the BY-2 cells, the effect of the (−228/−178) internal deletion in mesophyll protoplasts was dramatic. Indeed when the construct pΔC was used, GUS expression level dropped to 28%. The construct pΔD1 retained 57% of the activity of the full length promoter which was roughly the same as that of the construct pΔE (not tested in BY-2 cells). The activity of the ΔDE1 promoter was measured at 43% of the levels of the non-deleted CsVMV promoter.

In both protoplast systems, a dramatic decrease in gene expression was observed when the sequence from −222 to 176 was removed either by 5' deletion or by internal deletion. We can estimate that this region is responsible for about 60% of the promoter expression in protoplasts. The low activities of pD and pE are in some ways consistent with the histochemical data from transgenic plants in which these constructs displayed vascular-specific patterns of expression.

The construct pΔD1 consistently gave GUS activities above 50% of the full-length promoter. In leaf mesophyll protoplasts, this construct was in the same range of activity as pΔE though they exhibited very different levels of expression in plants. Similarly, the construct pΔDE1 gave high levels of expression that were not consistent with the results obtained in transgenic plants. Based on these results, we concluded that in protoplasts the regulatory mechanisms that govern the activity of the CsVMV promoter are different from those at work in plants. The (−222/−178) region plays a critical role in protoplasts while the region from −178 to −63 appears to be of lower importance in protoplast than in plants.

11. Discussion of Examples 9-10

Figure 12:
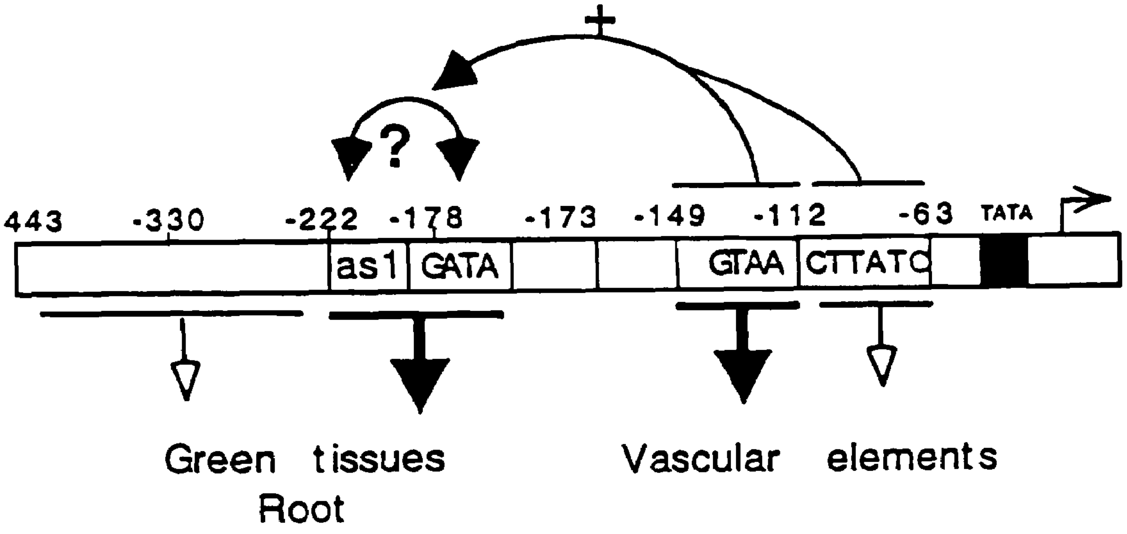
FIG. 12 illustrates a schematic representation of the functional map of the CsVMV promoter as described in Example 11. The numbers indicate relative positions and features using the transcription start site numbering system of FIG. 3. Vertical arrows indicate tissue specific functions, with the relative importance of the domain to that function indicated by the relative size of the arrow. Arrows at the top of the figure represent the synergistic interactions discussed in Example 11. Motifs as1, GATA and GTAA are identified and play important roles in promoter regulatory function.

This study was carried out to determine the functional structure of the CsVMV promoter. Different domains responsible for promoter expression in transgenic plants were identified by a deletion analysis of the regulatory region of the promoter. Our results showed that the constitutive pattern of expression of the CsVMV promoter is due to distinct tissue-specific domains. Moreover, synergistic interactions between elements are required for optimal promoter activity. All data from transgenic plants were combined to determine the first functional map of the CsVMV promoter as illustrated in FIG. 12. The region spanning from nucleotide −222 to −173 contains cis-elements that control promoter expression in green tissues and in root tips. As already described, Verdaguer et al, *Plant Mol Biol,* 31:1129-39, 1996, this region contains a consensus sequence of the activating sequence 1 (as1) identified in the 35S CaMV promoter, Lam et al, *Proc Natl Acad Sci USA,* 86:7890-4, 1989. In that promoter, the as1 element is directly involved in the root tip expression, Fromm et al, *Plant Cell,* 1:977-84, 1989, while it interacts with upstream elements to allow promoter activity in other tissues (Benfey & Chua, *Science,* 250:959-966, 1989; Fang et al, *Plant Cell,* 1:141-50, 1989; Benfey et al, *Embo Journal,* 9:1677-1684, 1990a; and Benfey et al, *Embo Journal,* 9:1685-96, 1990b). Lam et al, *Proc Natl Acad Sci USA,* 86:7890-4, 1989a, reported that mutation of this element in the 35S promoter leads to an 80% decrease of promoter activity in root and stems and an 50% decrease in leaves. Truncation of the CsVMV promoter to nucleotide −178 also emphasized the role of the as1 region for gene expression in root tips. The construct pΔDE1 (deletion of the 182/−63 region), which directed a GUS staining pattern that was restricted to the root tissues, had an intact as1 element. It was shown that as1 interacts with TGA1a, a bzip transcription factor from tobacco present mainly in root tissues Katagiri et al, *Nature,* 340:727-730, 1989; and Neuhaus et al, *Plant Cell,* 6:827-834, 1994. Consequently, the root expression pattern observed with the pΔDE1 construct could result from the interaction between TGA1a and the as1 sequence. However the pΔDE1 construct as well as the pΔD1 deletion (−182 to −112) showed that in the CsVMV promoter the as1 element on its own, cannot activate promoter expression in green tissues. On the other hand, we showed that the region from −182 to −173 is essential to direct promoter expression in mesophyll cells. Interestingly, this short region contains a GATA motif. The specific role of this GATA region independently of the as1 element cannot be assessed. Consequently, two hypothesis are conceivable: either the GATA region, on its own, controls promoter expression in green tissue, or the GATA region and the as1 element act together by synergy to control the CsVMV promoter activity in the mesophyll tissue. Published data reported that a GATA motif in the CaMV promoter, named activating sequence 2 (as2), Lam & Chua, *Plant Cell,* 1:1147-56, 1989, is also involved in leaf expression. Moreover the leaf expression controlled by this GATA region was dependent on sequences located within the −90 to −46 region of the 35S promoter (which contain the as1 element). The same type of interaction may control the CsVMV promoter expression in green tissue. However, the GATA motif identified in the CsVMV promoter is not identical with the as2 element of the CaMV promoter. We found a stronger homology with a GATA box identified in the rice tungro bacilliform badnavirus promoter, Yin & Beachy, *Plant J,* 7:969-980, 1995) which plays also an important role in the activation of this promoter. We also noted that in the CsVMV promoter the GATA motif resembles a box I consensus (GTAAPu) found in several light and circadian-clock-regulated promoters, Donald & Cashmore, *The Embo Journal,* 9:1717-1726, 1990; and Teakle and Key, *Plant Molecular Biology,* 29:1253-1266, 1995.

The constructs pΔDE2 and pΔDE3 which contain the as1 and GATA elements displayed a weak GUS expression pattern in transgenic plants. This data implied that one or more additional elements are required for promoter activation in green tissues. We observed that the regions from nucleotides −149 to −112 or the region from −112/−63 could restore promoter activity in mesophyll cells that was lost with the pΔDE2 and pΔDE3 constructs. These two regions could contain cis-acting elements with redundant functions that are necessary for promoter activation in green tissues. As it was shown by the construct pD or pE, these putative cis-elements are located in a promoter region that cannot direct gene expression in mesophyll cells. Synergistic or combinatorial mechanisms could prevail between the GATA region and the −149 to −63 region to allow expression in mesophyll cells. However, an alternative explanation can be proposed. We noted that the promoter is indeed active when at least 49 nucleotides are present between the GATA element (−182 to −173) and the position −63. The distance between the GATA region and the TATA box could be responsible of the results observed. A construct that includes a neutral linker keeping a correct distance between the GATA region and the TATA box would allow this question to be addressed. Nevertheless, in the CaMV 35S promoter, the as1 and GATA motifs are located between the positions −64 and −105, so much closer to the TATA box than in the CsVMV promoter. Thus, the smaller distance between the GATA region and TATA box created by the pΔDE2 and pΔDE3 internal deletions, should not prevent the activity of the as1 and GATA cis-elements. Additionally, results obtained with the construct pD, which is able to direct high level of gene expression in the vascular elements, clearly suggest that the region from −178 to −63 contains important cis-acting elements. Supporting this hypothesis, in vitro binding assays performed with the region −161 to −56 revealed a specific interaction with nuclear proteins. We detected only one retarded band, the formation of which was efficiently disrupted by competition with a 43 nucleotide fragment extending from nucleotide −141 to −99. It would have been more consistent with our in vivo data if two retarded complexes had been detected since both regions from −149 to −112 and from −112 to −63 play an active role in the activation process. It is possible that one specific binding cannot be detected due to a low concentration of transcriptional factors in our nuclear extract or to a lower affinity for the binding site or because cooperative binding with other factors is required. Sequence comparison analysis of the −149/−99 fragment with nucleotide database did not reveal any strong homologies. Examination of the nucleotide sequence of this fragment revealed the presence of a GTAA repeat located at positions −129 to −113. GTAA motifs have been found in various functional cis-acting elements such as the endosperm box of zein gene promoters, Maier et al, *The Embo Journal,* 6:17-22, 1987; and Muller & Knudsen, *Plant J,* 4:343-55, 1993, the as1 element and the OCS consensus, Ellis et al, *Plant J,* 4:433-43, 1993). The tef1 box of the promoters of the EF-1a genes of *Arabidopsis thaliania*, Curie et al, *Nucleic Acids Res,* 19:1305-1310, 1991; Curie et al, *Plant Mol Biol,* 18:1083-1089, 1992, and *Lycopersicon esculentum* contains also a GTAA repeat and shows similarities with the GTAA box of the CsVMV promoter. The tef1 box which is located in the −100 region of EF-1a promoters has been reported to be involved in promoter activation in cycling cells, Regad et al, *Mol Gen Genet,* 248:703-711, 1995. The role of the GTAA repeat in the CsVMV promoter will have to be further determined.

The expression of the CsVMV promoter in vascular elements is directed by the region encompassing nucleotides −178 to −63. This vascular domain contains two independent elements located respectively in the −149/−112 region and in the −112/−63 region. As mentioned earlier, Verdaguer et al, *Plant Mol Biol,* 31:1129-39, 1996, the latter contains a 22 nucleotide sequence, characterized by a CTTATC repeat, that is present in the same relative position (−78 to −100) in a vascular domain of the Commelina yellow mottle badnavirus promoter (ComYMV), Medberry & Olszewski, *Plant J,* 3:619-26, 1993. Our results suggest that the elements, involved in vascular expression of the CsVMV promoter, may be the ones that interact with the upstream mesophyll region. It is interesting to note that the vascular elements in the CsVMV promoter are located directly upstream of the TATA box. This arrangement is much like that reported for the RTBV and ComYMV promoters, Medberry & Olszewski, *Plant J,* 3:619-26, 1993; and Yin & Beachy, *Plant J,* 7:969-980, 1995. In the CaMV promoter as reported by Benfey et al, *Embo J,* 9:1685-96, 1990b, the vascular element is located in the B4 subdomain spanning nucleotides −310 to −209. Moreover in this promoter, the as1 element is also involved in the regulation of vascular expression. Deletion of the as1 region in the CsVMV did not affect the vascular expression. It is probable that the mechanisms which regulate vascular promoter activity in the CsVMV and the CaMV promoters are different.

In protoplasts, CsVMV promoter activity appeared to be controlled essentially by the region encompassing nucleotides −222 to −178 that contains the as1 consensus sequence. It is surprising to observe that expression from the promoter is independent of the sequence from −182 to −63. For instance in BY-2 protoplasts, we showed that the pΔDE promoter construct retained more than 80% of the wild-type promoter activity. Discrepancies of results between protoplast-based transient assays and transgenic plants were also mentioned for the 35S CaMV promoter, Fang et al, *Plant Cell,* 1:141-50, 1989; and Lam, *Results Probl Cell Differ,* 20:181-196, 1994. Ow et al, *Proceedings of the National Academy of Sciences of the USA,* 84:4870-4874, 1987, reported higher activity of a −90 truncated 35S CaMV promoter in carrot protoplasts than in transgenic plants. Similarly, we observed that the −90 derivative of the 35S promoter gave strong CAT activity in BY-2 protoplasts (data not shown) while it was reported that no CAT transcripts were detectable using the same construct in transgenic plants, Fang et al, *Plant Cell,* 1:141-50, 1989. Protoplasts are in a highly stressed physiological state, Roest et al, *Acta Botanica Neerlandica,* 42:1-25, 1993. The stress conditions could be responsible of activation or inactivation of various trans-acting factors interacting with the promoter. In this regard, several reports on the responsiveness of the as1 element to multiple stress related signal such as auxins, salicylic acid, methyl jasmonate are particularly relevant, Liu & Lam, *J Biol Chem,* 269:668-675, 1994; Qin et al, *The Plant Cell,* 6:863-874, 1994; Zhang & Singh, *Proc Natl Acad Sci USA,* 91:2507-11, 1994; and Xiang et al, *Plant Mol Biol,* 32:415-26, 1996.

We showed previously that in BY-2 protoplats, a CsVMV promoter construct encompassing nucleotides −368 to +20 was two fold less active than the full length promoter (−443 to +72), Verdaguer et al, *Plant Mol Biol,* 31:1129-39, 1996. The present study indicated that 5' terminal truncation of the promoter to position −222 did not affect the activity level. Indeed, in BY2 protoplasts, the construct pC retained more than 80% of the full length promoter activity. Consequently, the difference in promoter expression detected earlier is most probably due to the larger leader fragment. Untranslated viral leaders are usually known to influence messenger stability or translation initiation, Gallie & Walbot, *Nucleic Acids Res,* 20:4631-4638, 1992; and Dowson et al, *Plant Mol Biol,* 23:97-109, 1993. Recently, Chen et al, *J Virol,* 70:8411-8421, 1996, reported a direct effect of the RTBV leader on transcription activation. We cannot rule out the possibility of the presence of a such cis-acting sequence in CsVMV leader fragment.

The CsVMV promoter has a modular structure made of different domains that exert distinct influences on patterns of tissue specific expression. Moreover, promoter expression requires synergistic or combinatorial interactions between different cis-elements. These conclusions are reminiscent of those obtained with the CaMV 35S promoter, Benfey & Chua, *Science,* 250:959-966, 1990. It appears that the constitutive patterns of expression of the CaMV and CsVMV promoters are achieved through the same regulatory strategies. The similarity of their functional organization is emphasized by the common importance of the as1 and GATA cis-elements. However these two promoters are not entirely homologous in their functional structures. In the CsVMV promoter, the region extending from the position −63 to −149 contains essential elements for expression in plants. These elements were not identified in the CaMV 35S promoter and may indicate some divergence in the regulatory mechanisms used by these two caulimovirus promoters.

The foregoing written specification is considered to be illustrative of but not limiting the invention. Indeed, various modifications of the invention in addition to those shown and described herein will become apparent to those skilled in the art from the foregoing description and fall within the scope of the appended claims.

What is claimed is:

1. A transgenic plant comprising a promoter nucleotide sequence that is capable of initiating transcription of an operably linked heterologous nucleic acid sequence in a plant cell wherein said promoter nucleotide sequence has at least 80% identity to 18 sequential nucleotides of the cassava vein mosaic virus (CsVMV) promoter shown in SEQ ID NO 3 (pA) and is operatively linked to said heterologous nucleic acid sequence.

2. The transgenic plant of claim 1, wherein said promoter nucleotide sequence has at least 80% identity to SEQ ID NO:1 (CVP1) or SEQ ID NO:2 (CVP2).

3. The transgenic plant of claim 1, wherein said promoter nucleotide sequence has at least 80% identity to SEQ ID NO:3 (pA)

4. The transgenic plant of claim 1, wherein said promoter nucleotide sequence has at least 80% identity to SEQ ID NO:4 (pB), SEQ ID NO:5 (pC), SEQ ID NO:6 (pD), SEQ ID NO:7 (pE), SEQ ID NO:9 (pΔB), SEQ ID NO:10 (pΔC), SEQ ID NO:11 (pΔD1), SEQ ID NO:12 (pΔD2), SEQ ID NO:13 (pΔD3), SEQ ID NO:14 (pΔDE1), SEQ ID NO:15 (pΔDE2), SEQ ID NO:16 (pΔDE3), or SEQ ID NO:17 (pΔE).

5. The transgenic plant of claim 1, wherein said plant cell is a monocot or a dicot.

6. The transgenic plant of claim 1, wherein said transcription is initiated in a plant mesophyll tissue.

7. The transgenic plant of claim 1, wherein said transcription is initiated in a plant phloem tissue.

8. The transgenic plant of claim 1, wherein said transcription is initiated in a plant root tip tissue.

9. A transgenic plant comprising a CsVMV promoter nucleotide sequence and a heterologous nucleotide sequence, wherein said CsVMV promoter nucleotide sequence and said heterologous nucleotide sequence are operatively linked, and wherein said CsVMV promoter nucleotide sequence initiates transcription of said heterologous nucleic acid sequence in a cell of said transgenic plant.

10. The transgenic plant of claim 9, wherein said CsVMV promoter nucleotide sequence comprises SEQ ID NO:3 (pA).

11. The transgenic plant of claim 9, wherein said CsVMV promoter nucleotide sequence comprises SEQ ID NO:1 (CVP1).

12. The transgenic plant of claim 9, wherein said CsVMV promoter nucleotide sequence comprises SEQ ID NO:2 (CVP2).

13. A transgenic plant comprising a CsVMV promoter nucleotide sequence, wherein said CsVMV promoter nucleotide sequence consists essentially of SEQ ID NO:3.

14. A transgenic plant comprising a CsVMV promoter nucleotide sequence, wherein said CsVMV promoter nucleotide sequence does not include a naturally occurring CsVMV genomic sequence adjacent to said CsVMV promoter nucleotide sequence.

15. A transgenic plant comprising a recombinant CsVMV promoter nucleotide sequence.

16. The transgenic plant of claim 1 wherein the promoter nucleotide sequence has at least 90% identity to 18 sequential nucleotides of the cassava vein mosaic virus (CsVMV) promoter shown in SEQ ID NO 3 (pA).

17. The transgenic plant of claim 1 wherein the promoter nucleotide sequence has 100% identity to 18 sequential nucleotides of the cassava vein mosaic virus (CsVMV) promoter shown in SEQ ID NO 3 (pA).

* * * * *